United States Patent [19]

Gormley

[11] 4,421,744

[45] Dec. 20, 1983

[54] AMINOACYL DERIVATIVES

[75] Inventor: James J. Gormley, Holmes Chapel, United Kingdom

[73] Assignee: Imperial Chemical Industries PLC, London, England

[21] Appl. No.: 379,614

[22] Filed: May 18, 1982

[30] Foreign Application Priority Data

Jun. 22, 1981 [GB] United Kingdom ................. 8119163

[51] Int. Cl.³ ..................... A61K 37/00; C07C 103/52
[52] U.S. Cl. ............................. 424/177; 260/112.5 E
[58] Field of Search .................. 260/112.5 E; 424/177

[56] References Cited

U.S. PATENT DOCUMENTS

| | | | |
|---|---|---|---|
| 4,148,785 | 4/1979 | Dheer et al. | 424/177 |
| 4,148,786 | 4/1979 | Sarantakis | 424/177 |
| 4,178,371 | 12/1979 | Morgan | 424/177 |
| 4,199,568 | 4/1980 | Rance et al. | 260/112.5 E |
| 4,216,127 | 8/1980 | Sarantakis | 260/112.5 E |
| 4,216,128 | 8/1980 | Sarantakis | 424/177 |
| 4,254,106 | 3/1981 | Wilkinson | 424/177 |
| 4,261,888 | 4/1981 | Bauer et al. | 260/112.5 E |
| 4,278,596 | 7/1981 | Garsky | 424/177 |
| 4,320,051 | 3/1982 | Sarantakis | 260/112.5 E |
| 4,322,340 | 3/1982 | Shuman et al. | 260/112.5 E |
| 4,322,342 | 3/1982 | Smithwick, Jr. et al. | 260/112.5 E |

Primary Examiner—Delbert R. Phillips
Attorney, Agent, or Firm—Cushman, Darby & Cushman

[57] ABSTRACT

Peptide and pseudopeptide derivatives of the formula:

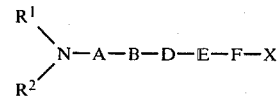

wherein $R^1$ and $R^2$ stand for defined hydrocarbyl or halo-hydrocarbyl substituents, for example alk-2-enyl radicals; =N—A— stands for a defined amino acid residue; B, D and E, which may be the same or different, stand for a valency bond or a defined amino acid residue; F stands for a defined amino acid residue; X stands for a carboxy, ester or amide group; and the linkages between the amino acid residues are peptide linkages or at least one of said linkages is a defined pseudo linkage; and pharmaceutically-acceptable salts thereof. Processes for the manufacture of the compounds. Pharmaceutical compositions comprising one of the compounds and a pharmaceutical diluent or carrier. The compounds are antagonists at the opiate receptors, and most of them are selective δ-receptor antagonists.

9 Claims, No Drawings

AMINOACYL DERIVATIVES

This invention relates to aminoacyl derivatives, and more particularly it relates to peptide and pseudopeptide derivatives which are active as antagonists at the so-called opiate receptors in warm-blooded animals.

It is generally recognised that in warm-blooded animals there are at least two distinct types of opiate receptor, i.e. the $\mu$-receptor and the $\delta$-receptor (see Robson & Kosterlitz, Proc. R. Soc. London (B), 1979, 205, 425–432, Goodman et al., Proc. Natl. Acad. Sci. U.S.A., 1980, 77, 6239–6243, and Simon, Trends in Pharmacol. Sci., 1981, 2, 155). Compounds are known, for example naloxone, which are antagonists of natural endogenous agonist substances for example enkephalins, at opiate receptors. However, all of these known antagonists are more potent at the $\mu$-receptors than at the $\delta$-receptors. That is, all of the known opiate antagonists are selective $\mu$-receptor antagonists.

The preparation of N-mono-allyl-[Leu]enkephalin and N-mono-allyl-[Met]enkephalin has been described by Hahn et al., Res. Commun. Chem. Pathol. Pharmacol., 1977, 18, 1, who stated that those compounds have both agonist and antagonist properties. Up to the present time there has been no description in the literature, including the patent literature, of an enkephalin or chemically similar compound in which the N-terminus bears two lower alkenyl or like substituents. We have found that such compounds are opiate antagonists which are virtually devoid of agonist properties, and, in contrast to the above-mentioned known antagonists, they are at least as potent at the $\delta$-receptors as they are the $\mu$-receptors, and most of them are more potent at the $\delta$-receptors than they are at the $\mu$-receptors. That is, most of them are selective $\delta$-receptor antagonists.

According to the invention there are provided compounds of the formula:

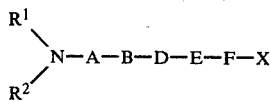

wherein:

$R^1$ stands for an alk-2-enyl, haloalk-2-enyl or alk-2-ynyl radical of not more than 5 carbon atoms, or a furylmethyl or tetrahydrofurylmethyl radical;

$R^2$ stands for an alk-2-enyl, haloalk-2-enyl, alk-2-ynyl or alkyl radical of not more than 5 carbon atoms, a phenylalkyl radical of not more than 10 carbon atoms, or a furylmethyl or tetrahydrofurylmethyl radical;

or $R^1$ and $R^2$ are joined to form, together with the adjacent nitrogen atom, a morpholino, piperidino, methylpiperidino or 1-aza-3,6-methancycloheptan-1-yl radical;

>N-A stands for the residue of D-, L-, D,L- or aza-tyrosine, phenylalanine or p-aminophenylalanine;

B stands for a single valency bond or for the residue of D-, L- or D,L-, where the amino acid contains a chiral centre, or aza-, glycine, methionine, alanine, serine or sarcosine;

D stands for a single valency bond or for the residue of D-, L- or D,L-, where the amino acid contains a chiral centre, or aza-, glycine, alanine, phenylalanine, sarcosine, serine, O-benzylserine, cysteine or S-benzylcysteine;

E stands for a single valency bond or for the residue of D-,L- or D,L-, where the amino acid contains a chiral centre, or aza-, glycine, phenylalanine, N-methylphenylalanine, p-nitrophenylalanine, p-chlorophenylalanine or tryptophan;

F stands for the residue of D-,L- or D,L-, where the amino acid contains a chiral centre, or aza-, glycine, leucine, methionine, alanine, phenylalanine, proline, serine, O-benzylserine or norleucine, or a dipeptide residue which is D-,L-, D,L- or aza-, leucine-arginine, leucine-glutamic acid, leucine-leucine, leucine-phenylalanine or leucine-threonine; and X stands for a group of the formula $-CO_2R^3$ or $-CONHR^4$, wherein $R^3$ stands for hydrogen or an alkyl or alkenyl radical of not more than 4 carbon atoms, and $R^4$ stands for hydrogen, an alkyl, hydroxyalkyl, cycloalkyl or alkoxycarbonylalkyl radical of not more than 6 carbon atoms, a phenylalkyl or phenyl(hydroxy)alkyl radical of not more than 9 carbon atoms, or a phenyl, phenylcyclopropyl, 2-benzylthioethyl, 2-(2-phenylethylthio)ethyl or indanyl radical;

and wherein the linkages between the amino acid residues are peptide linkages or at least one of said linkages is a pseudo linkage selected from $-CH_2S-$, $-NHCO-$, $-CO.NH.O-$, trans-$CH=CH-$ and $-CH_2CH_2-$;

and pharmaceutically-acceptable salts thereof.

It is to be understood that throughout this specification the standard abbreviations for amino acids are used (see Pure and Applied Chemistry, 1974, 40, 317–331, and Neuropeptides, 1981, 1, 231–235). An $\alpha$-aza-amino-acid is one in which the $\alpha$-CH part of the amino acid has been replaced by a nitrogen atom. The abbreviation for an $\alpha$-aza-amino-acid is derived from that for the corresponding amino acid by adding the prefix "Az". Thus, for example, Azala stands for $\alpha$-aza-alanine, Azgly stands for $\alpha$-aza-glycine, and so on. When the configuration of an amino acid is not designated herein, it is to be understood that it has the natural L configuration (except for acids having no chiral centre). In this specification the word "pseudo" has the meaning that, in the compound in question, at least one of the conventional peptide linkages ($-CO.NH-$) has been replaced by a linkage selected from $-CH_2S-$, $-NHCO-$, $-CO.N-H.O-$, trans-$CH=CH-$ and $-CH_2CH_2-$. The change from the peptide linkage is indicated by the use of the Greek symbol psi ($\psi$); see Neuropeptides, 1981, 1, 231–235. It is to be understood that in the compounds of this invention any particular chiral centre may be in the D-, L- or D,L-configuration.

$R^1$ may, for example, stand for an allyl, crotonyl, 2-chloroallyl, 3-chloroallyl, propargyl, 2-furylmethyl, 3-furylmethyl or 2-tetrahydrofurylmethyl radical.

$R^2$ may, for example, stand for an allyl, crotonyl, 2-chloroallyl, 3-chloroallyl, propargyl, methyl, ethyl, n-propyl, n-butyl, benzyl, 2-phenylethyl, 2-furylmethyl, 3-furylmethyl or 2-tetrahydrofurylmethyl radical.

Alternatively, $R^1$ and $R^2$ may be joined to form, together with the adjacent nitrogen atom, a morpholino, piperidino, 4-methylpiperidino, 3-methylpiperidino or 1-aza-3,6-methancycloheptan-1-yl radical.

>N-A may, for example, stand for Tyr or Phe(p-$NH_2$).

B may, for example, stand for a single valency bond or Gly, Azgly, D-Met, D-Ala, D-Ser or Sar.

D may, for example, stand fo a single valency bond or Gly, Azgly, Ala, D-Ala, Azala, Phe, D-Phe, Sar, D,L-Ser, Ser, Ser(Bzl), D-Ser(Bzl) or D,L-Cys(Bzl).

E may, for example, stand for a single valency bond or Gly, Phe, D-Phe, Azphe, MePhe, Phe(p-NO$_2$), D,L-Phe(p-Cl) or Trp.

F may, for example, stand for Gly, Azgly, Leu, D-Leu, D,L-Leu, Met, D-Ala, Phe, Pro, Ser, Ser(Bzl), Nle, Leu-Arg, Leu-Glu, Leu-D-Glu, Leu-Leu, Leu-Phe or Leu-Thr.

$R^3$ may, for example, stand for hydrogen or a methyl, ethyl or allyl radical.

$R^4$ may, for example, stand for hydrogen or an ethyl, 4-methyl-2-pentyl, 1-hydroxy-4-methyl-2-pentyl, cyclohexyl, 3-(ethoxycarbonyl)propyl, 2-methoxycarbonyl-2-butyl, benzyl, 2-phenylethyl, 3-phenylpropyl, 1-phenyl-2-propyl, R-1-phenyl-2-propyl, 2-phenylpropyl, 1-hydroxy-3-phenyl-2-propyl, phenyl, phenylcyclopropyl, 2-benzylthioethyl, 2-(2-phenylethylthio)ethyl or 1-indanyl radical.

One preferred embodiment of the invention consists of compounds of the formula I wherein $R^1$ and $R^2$ stand for allyl radicals, >N-A stands for Tyr, and B, D, E, F and X have the meanings stated above, all of the linkages between the amino acid residues or α-aza-amino-acid residues are peptide linkages or one of said linkages is a pseudo linkage selected from —CH$_2$S—, —NH-CO—, —CO.NH.O—, trans—CH=CH— and —CH$_2$CH$_2$—, and pharmaceutically-acceptable salts thereof.

A group of preferred compounds of the invention consists of diallyl-Tyr-Gly-Gly-ψ(CH$_2$S)-Phe-Leu-OH, diallyl-Tyr-Gly-Azgly-Phe-Leu-OH, diallyl-Tyr-Gly-Gly-Phe-ψ(NHCO)-D,L-Leu-OEt, diallyl-Tyr-Gly-Azgly-Phe-Leu-D-Glu-OH, and

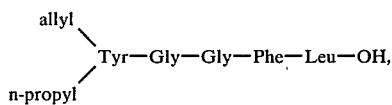

and pharmaceutically-acceptable salts thereof.

The salts of the invention may, in the case where the compound of the formula I is sufficiently basic, be pharmaceutically-acceptable acid-addition salts or, in the case where the said compound is sufficiently acidic, pharmaceutically-acceptable base-addition salts. The acid-addition salts are derived from an inorganic or organic acid which affords a pharmaceutically-acceptable anion, for example hydrochloric, phosphoric, acetic, citric or trifluoroacetic acid. The base-addition salts are derived from a base which affords a pharmaceutically-acceptable cation, for example ammonia, N-methyl-D-glucosamine or arginine, or they may, for example, be alkali metal salts.

The compounds of the invention can be prepared by procedures which are conventional in peptide chemistry.

According to a further feature of the invention there is provided a process for the manufacture of the compounds of the formula I, wherein $R^1$, $R^2$, A, B, D, E, F and X have the meanings stated above, and pharmaceutically-acceptable salts thereof, which comprises removing one or more conventional protecting groups from a corresponding protected compound by conventional means.

In the case where >N-A stands for Tyr, D-Tyr and D,L-Tyr, the protecting group may be a t-butyl radical which may be removed by treatment of the protected derivative with hydrogen chloride or trifluoroacetic acid. Hydrogen chloride may be used in the form of an aqueous solution, at a concentration between 1 M and that of a saturated solution, or it may be used as a solution in an organic solvent, for example ethyl acetate, at a concentration in the range 2 M to 6 M. The process is preferably carried out at a temperature between 0° C. and ambient temperature, and optionally in the presence of a scavenger compound, for example anisole, thioanisole, methionine or dimethyl sulphide. Trifluoroacetic acid may be used as a de-protecting agent by itself or it may be diluted with 5–10% by volume of water. The process involving trifluoroacetic acid is preferably carried out at ambient temperature, and optionally in the presence of a scavenger compound, for example 2-mercaptoethanol or anisole.

According to a further feature of the invention there is provided a process for the manufacture of those of the compounds of the formula I wherein X stands for a carboxy radical, and pharmaceutically-acceptable salts thereof, which comprises hydrolysing a corresponding (1–6C)alkyl or benzyl ester under alkaline conditions.

A suitable ester is a methyl, ethyl or benzyl ester. A suitable hydrolytic agent is an alkali metal hydroxide, for example sodium hydroxide. The hydrolysis is carried out in the presence of water, and preferably in the presence of methanol or ethanol. The hydrolysis is conveniently carried out at ambient temperature.

According to a further feature of the invention there is provided a process for the manufacture of those of the compounds of the formula I which are amides containing the group —CONHR$^4$, wherein $R^4$ has the meaning stated above, and pharmaceutically-acceptable salts thereof, which comprises reacting a corresponding carboxylic acid or (1–4C)alkyl ester thereof with a compound of the formula $R^4NH_2$.

The process is conveniently carried out in methanol or ethanol.

According to a further feature of the invention there is provided a process for the manufacture of those of the compounds of the formula I which contain the group:

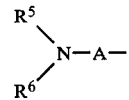

II wherein $R^5$ and $R^6$, which may be the same or different, stand for an alk-2-enyl, haloalk-2-enyl or alk-2-ynyl radical of not more than 5 carbon atoms, and pharmaceutically-acceptable salts thereof, which comprises reacting the corresponding compound containing the group:

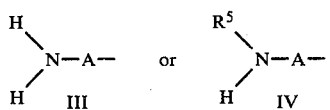

with a compound of the formula $R^5$Hal or $R^6$Hal, wherein $R^5$ and $R^6$ have the meanings stated above and Hal stands for a halogen atom, in the presence of an acid-binding agent, and wherein >N-A- has the meaning stated above.

Hal may, for example, stand for a chlorine or bromine atom. A suitable acid-binding agent is, for example, an alkali metal carbonate or bicarbonate, for example potassium carbonate or sodium bicarbonate. The process is conveniently carried out in aqueous ethanol, at an elevated temperature. It is to be understood that, by varying the conditions of the reaction and/or the amounts of the reactants, it is possible to obtain products containing two identical N-substituents or containing two different N-substituents (in the latter case by first making the $R^5$-NH-A- compound and then converting it into the $R^5$-$NR^6$-A- compound).

According to a further feature of the invention there is provided a process for the manufacture of those of the compounds of the formula I which contain the group:

wherein $R^7$ stands for a furylmethyl or tetrahydrofurylmethyl radical and $R^8$ stands for an alkyl radical of not more than 5 carbon atoms, a phenylalkyl radical of not more than 10 carbon atoms, or a furylmethyl or tetrahydrofurylmethyl radical, and pharmaceutically-acceptable salts thereof, which comprises reacting the corresponding compound containing the group:

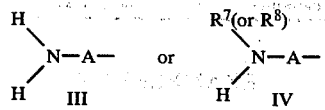

with the appropriate aldehyde or ketone and an alkali metal hydride reducing agent, and wherein >N-A- has the meaning stated above.

The aldehyde or ketone may, for example, be propionaldehyde, 2-furaldehyde, benzaldehyde or acetone. The alkali metal hydride may, for example, be an alkali metal borohydride, for example sodium cyanoborohydride. The process is conveniently carried out in ethanol, optionally together with acetic acid, at ambient temperature. It is to be understood that, by varying the conditions of the reaction and/or the amounts of the reactants, it is possible to obtain products containing two identical N-substituents or containing two different N-substituents (in the latter case by first making the $R^7$-NH-A-compound and then converting it into the $R^7$-$NR^8$-A-compound).

Compounds of the formula I containing the group:

wherein $R^5$ and $R^8$ have the meanings stated above, and pharmaceutically-acceptable salts thereof, can be obtained by reacting the corresponding compound containing the group of the formula III with $R^5$Hal in the presence of an acid-binding agent, as described above, so as to obtain a compound containing the group of the formula IV, and then reacting the latter compound with the appropriate aldehyde or ketone and an alkali metal hydride reducing agent so as to obtain the desired product. Alternatively, the order of these two reactions can be reversed.

The peptide and pseudopeptides used as starting materials in the processes of the invention can be prepared by procedures which are conventional in peptide chemistry, as is illustrated hereinafter by the descriptions of the preparation of various starting materials and by the reaction diagrams. Similarly, the pharmaceutically-acceptable salts of the invention are obtainable by conventional procedures.

The activity of the compounds of the invention as antagonists at opiate receptors has been demonstrated in the guinea pig ileum test ("ileum test") and the mouse vas deferens test ("vas test"); see the article by Shaw et al. in "Characteristics and Functions of Opioids", edited by Van Ree and Terenius, Elsevier/North-Holland Biomedical Press, 1978, 185–195. It is generally recognised that in the guinea pig ileum the $\mu$-receptor predominates, and that in the mouse vas deferens the $\delta$-receptor predominates. The potency of a compound in the above-mentioned tests is expressed as a Ke value, i.e. the concentration of the compound (antagonist) in the presence of which the agonist concentration has to be doubled in order to maintain a constant response. [Leu]-enkephalin is used as the agonist in both tests. The potency of any particular compound in the tests depends upon its precise chemical structure, but the compounds of the invention are active in the ileum test at a concentration in the range 1 $\mu$M to 30 $\mu$M, and in the vas test at a concentration in the range 10 nM to 10 $\mu$M ($\mu$M stands for micromole, i.e. $10^{-6}$ mole, and nM stands for nanomole, i.e. $10^{-9}$ mole).

Data illustrating the lack of toxicity of a compound of the invention, namely: $(allyl)_2$>Tyr-Gly-Gly-$\psi$($CH_2S$)-Phe-Leu-OH is as follows:

(1) When administered subcutaneously, the compound exhibits no toxic effects at doses up to 100 mg./kg. in the rat.

(2) In male and female mice, subcutaneous doses of up to 100 mg./kg. have been administered without significant toxic effect.

(3) An intravenous dose of 100 mg./kg. (which is a very high dose) in the mouse produced no toxic effects.

(4) The compound has been administered orally to rats at 150 mg./kg. without producing any toxic effects.

Because of their activity as opiate receptor antagonists, the compounds of the invention may be used for the treatment of the following conditions and/or diseases in man: schizophrenia and other mental illnesses, stress, shock, anorexia nervosa, epilepsy, disorders of the endocrine function including post-menopausal flushing, and gastro-intestinal disorders. The compounds may also be used as sedatives. When a compound of the invention is used for the treatment of man, it may be administered orally, or parenterally, for example by intraveous, subcutaneous or intramuscular injection or by infusion, or sub-lingually or rectally. A recommended daily oral dose for man is in the range 1 mg. to 1.0 g. Such a dose may be administered as a single daily dose or it may be divided into, for example, three doses per day. A recommended parenteral dose for man is 1 mg. to 250 mg., a recommended sub-lingual dose is 1 mg. to 250 mg., and a recommended rectal dose is 2 mg. to 1.0 g.

The compounds of the invention may also be used as research tools or diagnostic agents in pharmacological or related studies.

According to a further feature of the invention there are provided pharmaceutical compositions comprising a compound of the formula I, wherein $R^1$, $R^2$, A, B, D, E, F and X have the meanings stated above, or a pharmaceutically-acceptable salt thereof, and a pharmaceutically-acceptable diluent or carrier.

The pharmaceutical compositions of the invention may be in a form suitable for oral, parenteral, sub-lingual or rectal administration. Thus, for example, they may be in an orally-administrable unit dosage form, for example tablets or capsules, which may optionally be adapted for sustained or controlled release, or they may be in an injectable form, for example a sterile injectable solution or suspension, or in the form of a suppository. The pharmaceutical compositions of the invention are obtainable in conventional manner using conventional diluents or carriers.

The pharmaceutical compositions of the invention may optionally contain, in addition to a peptide or pseudopeptide derivative of the invention:

(1) a known opiate antagonist, for example naloxone;
(2) a known psychotropic agent, for example an antipsychotic agent, for example chlorpromazine, or a antidepressant agent, for example imipramine, or an anxiolytic agent, for example chlordiazepoxide;
(3) a known analgesic agent, for example morphine; or
(4) a known anticonvulsant agent, for example primidone.

The invention is illustrated but not limited by the following Examples, in which the $R_f$ values refer to ascending thin layer chromatography on silica gel plates (Kieselgel G). The solvent systems used, unless otherwise stated, were as follows (the ratios are by volume):

| | |
|---|---|
| $R_fA$ | n-butanol/acetic acid/water (4:1:5) |
| $R_fB$ | n-butanol/acetic acid/water/pyridine (15:3:12:10) |
| $R_fC$ | s-butanol/3% w/v aqueous ammonium hydroxide (3:1) |
| $R_fD$ | acetonitrile/water (3:1) |
| $R_fH$ | cyclohexane/ethyl acetate/methanol (1:1:1) |
| $R_fK$ | chloroform/methanol/water (55:40:10) |
| $R_fK'$ | chloroform/methanol/water (55:40:1) |
| $R_fK_{HOAc}$ | chloroform/methanol/acetic acid (60:30:5) |
| $R_fK_{NH_3}$ | chloroform/methanol/ammonium hydroxide (S.G. 0.880) (60:30:5) |
| $R_fL$ | methanol/ethyl acetate (5:95) |
| $R_fM$ | methanol/ethyl acetate (7:93) |
| $R_fP$ | chloroform/methanol (19:1) |
| $R_fP_{NH_3}$ | chloroform/methanol (19:1) containing 1% v/v ammonium hydroxide (S.G. 0.880) |
| $R_fQ$ | chloroform/methanol (9:1) |
| $R_fQ_{HOAc}$ | chloroform/methanol (9:1) containing 1% v/v acetic acid |
| $R_fQ_{NH_3}$ | chloroform/methanol (9:1) containing 1% v/v ammonium hydroxide (S.G. 0.880) |
| $R_fR$ | chloroform/methanol (4:1) |
| $R_fR_{HOAc}$ | chloroform/methanol (4:1) containing 1% v/v acetic acid |
| $R_fS$ | chloroform/methanol (7:3) |
| $R_fT$ | chloroform/methanol (6:4) |

The symbol D,L-indicates that the product in question was obtained as a mixture of diastereoisomers containing not less than 30% of any one diasteroisomer, the remainder of the mixture consisting of the other diasteroisomer.

In the footnotes column in the Tables hereinafter, there is a reference if the preparation of the starting material is described in another Example, or described in detail in the "Preparation of Starting Materials" section (SM1 to SM9), or outlined in a diagram (indicated by the letter D followed by the number of the appropriate Example).

The following abbreviations are used in this specification:

| | | | |
|---|---|---|---|
| Me | methyl | OCP | 2,4,5-trichlorophenoxy |
| Et | ethyl | DCCI | dicyclohexylcarbodiimide |
| $Pr^n$ | n-propyl | DCHA | dicyclohexylamine |
| $Pr^i$ | isopropyl | DMF | dimethylformamide |
| $Bu^n$ | n-butyl | mM | millimole |
| $Bu^i$ | isobutyl | NCDI | N—carbonyldiimidazole |
| $Bu^t$ | t-butyl | NMR | nuclear magnetic resonance |
| Ph | phenyl | TFA | trifluoroacetic acid |
| Bzl | benzyl | THF | tetrahydrofuran |
| OSu | 1-succinimidolyloxy | t.l.c. | thin layer chromatography |
| Boc | t-butoxycarbonyl | Z | benzyloxycarbonyl |

EXAMPLES 1–72

The protecting group(s) in the protected polypeptide or pseudopeptide was or were removed by cleavage with TFA using one of the procedures A1 to A5 described below. The products thus obtained are listed in Table I.

A1. The starting material (ca. 0.2 g.) was dissolved in sufficient TFA containing 5 to 10% v/v of water to give an approximately 10% w/v solution. The mixture was stirred at 20° to 25° C. for 0.5 to 2 hours, and the product was isolated by evaporation of the solvent in vacuo.

A2. As A1, but using a 2:1 v/v mixture of TFA and anisole.

A3. As A1, but in the presence of 5 molecular equivalents of methionine per molecular equivalent of starting material.

A4. As A1, but in the presence of 10 molecular equivalents of dimethyl sulphide per molecular equivalent of starting material.

A5. As A1, but using a 2:1 v/v mixture of TFA and thioanisole.

TABLE I

| Example No. | Product | $R_f \times 10^2$ A | B | C | D | H | P | Q | Other | Process | Footnotes |
|---|---|---|---|---|---|---|---|---|---|---|---|
| 1 | allyl\\Tyr—Gly—Gly—Phe—Leu—Arg—OH/allyl | 34 | 66 | 21 | | | | | K80 | A1 | 2,6 freeze-dried D1 |

TABLE I-continued

| Example No. | Product | $R_f \times 10^2$ A | B | C | D | H | P | Q | Other | Process | Footnotes |
|---|---|---|---|---|---|---|---|---|---|---|---|
| 2 | allyl\Tyr—Gly—Gly—Phe—Leu—Glu—OH /allyl | 46 | 50 | 17 | 60 | | | | | A1 | 1,8 D2 |
| 3 | allyl\Tyr—Gly—Azgly—Phe—Leu—Glu—OH /allyl | 53 | 60 | 17 | | | | | K85 | A1 | 1 |
| 4 | allyl\Tyr—Gly—Azgly—Phe—Leu—D-Glu—OH /allyl | | | | 67 | 32 | | | K33 | A1 | 1 |
| 5 | allyl\Tyr—Gly—Azgly—Phe—Leu—Leu—OH /allyl | 66 | 66 | 40 | 65 | | | | K73 | A1 | 1 |
| 6 | allyl\Tyr—Gly—Azgly—Phe—Leu—Thr—OH /allyl | 40 | 63 | 33 | 73 | | | | K68 | A1 | 4 D6 |
| 7 | allyl\Tyr—Gly—Azgly—Phe—Leu—Phe—OH /allyl | 57 | 66 | | | | | | K'69 | A1 | 1 |
| 8 | allyl\Tyr—Gly—Gly—Phe—Leu—OMe /allyl | | | | | | 8 | 16 | K95 | A1 | 3,6 |
| 9 | allyl\Tyr—Gly—D,L-Ser—Phe—Leu—OMe /allyl | | | | | | | | $Q_{HOAc}45$ | A1 | 3,14 |
| 10 | allyl\Tyr—Gly—D,L-Ser—Phe—Leu—OH /allyl | | | | | | | | $R_{HOAc}33$ | A1 | 3,15 |
| 11 | $CH_2=CCl.CH_2$\Tyr—Gly—Gly—Phe—Leu—OH /allyl | | | | | | | | R17 | A1 | 1 |
| 12 | allyl\Tyr—Azgly—Gly—Phe—Leu—OH /allyl | 75 | 40 | 80 | 85 | | | | | A1 | 23 |
| 13 | allyl\Tyr—D-Met—Gly—Phe—Leu—OMe /allyl | | | | | | 25 | 49 | K'78 | A3 | 3,15 D13 |
| 14 | allyl\Tyr—D-Ala—Gly—Phe—Leu—OMe /allyl | | | | | | | 42 | | A3 | 17 |
| 15 | allyl\Tyr—D-Ala—Gly—Phe—Leu—OH /allyl | | | | | | | 0 | K'59 | A1 | 3,7 |

TABLE I-continued

| Example No. | Product | A | B | C | D | H | P | Q | Other | Process | Footnotes |
|---|---|---|---|---|---|---|---|---|---|---|---|
| 16 | allyl<br>    \<br>      Tyr—D-Ser—Gly—Phe—Leu—OMe<br>    /<br>allyl | | | | | | | 25 | K'78 | A1 | 3,10,17<br>D16 |
| 17 | allyl<br>    \<br>      Tyr—Sar—Azgly—Phe—Leu—OH<br>    /<br>allyl | 42 | 62 | 36 | 75 | | | | | A1 | 1,16 |
| 18 | allyl<br>    \<br>      Tyr—Azgly—Azgly—Phe—Leu—OH<br>    /<br>allyl | 57 | 60 | 34 | 53 | | | | | A1 | 1<br>D18 |
| 19 | $CH_2=CCl.CH_2$<br>    \<br>      Tyr—Gly—Gly—Phe—Leu—OH<br>    /<br>$CH_2=CCl.CH_2$ | | | | | | | | S35 | A1 | 1 |
| 20 | $CH_2=CCl.CH_2$<br>    \<br>      Tyr—Gly—Gly—Phe—Leu—OH<br>    /<br>$Pr^n$ | | | | | | | | T47 | A1 | 1 |
| 21 | ClCH=CH.CH$_2$<br>  cis<br>    \<br>      Tyr—Gly—Gly—Phe—Leu—OH<br>    /<br>ClCH=CH.CH$_2$<br>  cis | | | | | | | | T46 | A1 | 1 |
| 22 | allyl<br>    \<br>      Tyr—D-Ser—Gly—Phe—D-Leu—OMe<br>    /<br>allyl | | | | | | | 36 | K89<br>K'85 | A1 | 3,15 |
| 23 | allyl<br>    \<br>      Tyr—Gly—Azgly—Phe—Leu—OMe<br>    /<br>allyl | 66 | 76 | 77 | | | | | | A1 | 3 |
| 24 | allyl<br>    \<br>      Tyr—Gly—Azgly—Phe—Leu—OH<br>    /<br>allyl | 60 | 70 | 40 | 77 | | | | | A1 | 3,11<br>SM5 |
| 25 | allyl<br>    \<br>      Tyr—Gly—Azgly—Phe—Leu—NH$_2$<br>    /<br>allyl | 56 | 76 | 71 | | | | | | A1 | 3<br>D25 |
| 26 | allyl<br>    \<br>      Tyr—Gly—Ala—Phe—Leu—OH<br>    /<br>allyl | | | | | | | | R29 | A2 | 3,15 |
| 27 | allyl<br>    \<br>      Tyr—Gly—D-Ala—Phe—Leu—OH<br>    /<br>allyl | | | | | | | | R27 | A2 | 3,10<br>SM9 |
| 28 | allyl<br>    \<br>      Tyr—Gly—Azala—Phe—Leu—OH<br>    /<br>allyl | | | | | | | 33 | K'65 | A1 | 1<br>D25 |

TABLE I-continued

| Example No. | Product | A | B | C | D | H | P | Q | Other | Process | Footnotes |
|---|---|---|---|---|---|---|---|---|---|---|---|
| 29 | CH₃CH=CH.CH₂ (trans), CH₃CH=CH.CH₂ (trans) \ Tyr—Gly—Gly—Phe—Leu—OH | | | | | | | | T52 | A1 | 1 |
| 30 | allyl \ Tyr—ψ(CH₂S)—Gly—Gly—Phe—Leu—OMe / allyl | | | | | | | | P50 | A4 | 3,14 D30 |
| 31 | allyl \ Tyr—Gly—D-Phe—Phe—Leu—OMe / allyl | | | | 84 | 76 | 20 | 58 | | A1 | 1 |
| 32 | allyl \ Tyr—Gly—Azgly—D-Phe—Leu—OH / allyl | | | 58 | 68 | 43 | 70 | | K90 | A1 | 1,16 D32 |
| 33 | allyl \ Tyr—Gly—Azgly—Azphe—Leu—OH / allyl | | | 44 | 64 | 36 | 68 | | K68 | A1 | 3 D33 |
| 34 | allyl \ Tyr—Gly—Azgly—Phe—Pro—NH₂ / allyl | | | | | 70 | | 20 | K'80 | A1 | 3 |
| 35 | allyl \ Tyr—Gly—Azgly—Phe—Nle—OMe / allyl | | | | | 83 | 80 | 0 | 20 | A1 | 1 |
| 36 | allyl \ Tyr—Gly—Azgly—Phe—NHC(Me)Et.CO₂Me / allyl | | | | | 80 | 80 | | 13 | A1 | 2 |
| 37 | allyl \ Tyr—Gly—Phe—Gly—Leu—OH / allyl | | | 43 | 66 | 40 | | | K80 | A1 | 1 |
| 38 | allyl \ Tyr—Gly—Gly—MePhe—Leu—OH / allyl | | | 71 | 70 | 33 | | | K80 | A1 | 3,8 |
| 39 | allyl \ Tyr—Gly—Gly—Trp—Leu—OH / allyl | | | 66 | 70 | 36 | 78 | | 6 K'84 | A1 | 1 |
| 40 | allyl \ Tyr—Gly—Gly—Phe(p-NO₂)—Leu—OMe / allyl | | | | | | | | 33 K84 | A1 | 1 |
| 41 | allyl \ Tyr—Gly—Gly—D,L-Phe(p-Cl)—Leu—OMe / allyl | | | | | | | | streak K'80 38 | A1 | 1 |
| 42 | allyl \ Tyr—Gly—Gly—Phe—Pro—NH₂ / allyl | | | | | | | | K77 K'67 | A1 | 3 |

TABLE I-continued

| Example No. | Product | $R_f \times 10^2$ A | B | C | D | H | P | Q | Other | Process | Foot-notes |
|---|---|---|---|---|---|---|---|---|---|---|---|
| 43 | allyl\Tyr—Gly—Gly—Phe—Met—OMe/allyl | | | | | | 5 | 39 | | A1 | 1 |
| 44 | allyl\Tyr—Gly—Gly—ψ(CH₂S)—Phe—Leu—OH/allyl | | | | | | | 32 | R53 | A2 | 2,14 D44 |
| 45 | allyl\Tyr—Gly—Gly—ψ(CH₂S)—D-Phe—Leu—OH/allyl | | | | | | | 26 | R43 | A2 | 2,14 |
| 46 | allyl\Tyr—Gly—Gly—ψ(CH₂S)—Phe—Leu—OMe/allyl | | | | | | | | K91 K'71 | A2 | 3,9 SM7 |
| 47 | allyl\Tyr—Gly—ψ(CH₂CH₂)—Gly—Phe—Leu—OH/allyl | 66 | 70 | 45 | 70 | | | | K78 | A1 | 3,10 D47 |
| 48 | allyl\Tyr—Gly—Gly—ψ(CO.NH.O)—Phe—Leu—OH/allyl | 60 | 66 | 38 | 68 | | | | K'68 | A1 | 3,12 D48 |
| 49 | allyl\Tyr—Gly—Gly—Phe—ψ(NHCO)—D,L-Leu—OEt/allyl | 79 | 87 | 74 | | | | | K93 | A1 | 1 SM6 |
| 50 | allyl\Tyr—D-Ala—Gly—Phe—OMe/allyl | | | | | | 12 | 38 | K83 K'74 | A1 | 3 |
| 51 | allyl\Phe(p-NH₂)—Gly—Gly—Phe—Leu—OH/allyl | | | | 68 | 29 | | | K66 K'66 | A5 | 1 D51 |
| 52 | allyl\Tyr—Gly—Gly—Phe—NHcyclohexyl/allyl | 78 | | 79 | | | | | K93 | A2 | 3,14 D52 |
| 53 | allyl\Tyr—Gly—Gly—Phe—D,L-NHCHMeBuⁱ/allyl | 61 | 70 | 63 | | | | | | A2 | 3,10 |
| 54 | allyl\Tyr—Gly—NHCH₂CH₂SCH₂Ph/allyl | | | | | | | 47 | R78 | A1 | 1,13 |
| 55 | propargyl\Tyr—Gly—Gly—Phe—Leu—OH/propargyl | | | | | | | | K55 | A1 | 1 SM2 |
| 56 | allyl\Tyr—Gly—Gly—Phe—Leu—OH/Prⁿ | | | | | | | | T36 | A1 | 1 SM3 |

TABLE I-continued

| Example No. | Product | \multicolumn{8}{c}{$R_f \times 10^2$} | Process | Foot-notes |
| --- | --- | --- | --- | --- | --- | --- | --- | --- | --- | --- | --- |
| | | A | B | C | D | H | P | Q | Other | | |
| 57 | allyl\Me/Tyr—Gly—Gly—Phe—Leu—OH | | | | | | | | A35 | A1 | 1 SM3 |
| 58 | allyl\Pr$^i$/Tyr—Gly—Gly—Phe—Leu—OH | | | | | | | | T38 | A1 | 1 SM3 |
| 59 | allyl\Bu$^n$/Tyr—Gly—Gly—Phe—Leu—OH | | | | | | | | T38 | A1 | 1 SM3 |
| 60 | allyl\phenylethyl/Tyr—Gly—Gly—Phe—Leu—OH | | | | | | | | T41 | A1 | 1 SM3 |
| 61 | allyl\2-tetrahydrofurylmethyl/Tyr—Gly—Gly—Phe—Leu—OH | | | | | | | | T37 | A1 | 1 SM3 |
| 62 | 2-furylmethyl\Et/Tyr—Gly—Gly—Phe—Leu—OH | | | | | | | | T33 | A1 | 1 SM4 |
| 63 | 2-furylmethyl\Bu$^n$/Tyr—Gly—Gly—Phe—Leu—OH | | | | | | | | T32 | A1 | 1 SM4 |
| 64 | 3-furylmethyl\Pr$^n$/Tyr—Gly—Gly—Phe—Leu—OH | | | | | | | | M41 | A1 | 1 SM4 |
| 65 | 3-furylmethyl\3-furylmethyl/Tyr—Gly—Gly—Phe—Leu—OH | | | | | | | | T36 | A1 | 1 SM4 |
| 66 | 2-tetrahydrofurylmethyl\Pr$^n$/Tyr—Gly—Gly—Phe—Leu—OH | | | | | | | | T40 | A1 | 1 SM4 |
| 67 | 2-tetrahydrofurylmethyl\2-tetrahydrofurylmethyl/Tyr—Gly—Gly—Phe—Leu—OH | | | | | | | | T48 | A1 | 1 SM4 |
| 68 | (CH$_2$)$_5$ ring—N—Tyr—Gly—Gly—Phe—Leu—OH | | | | | | | | K'50 | A1 | 1 SM4 |
| 69 | (CH$_2$)$_2$\CHMe\(CH$_2$)$_2$—N—Tyr—Gly—Gly—Phe—Leu—OH | | | | | | | | K59 | A1 | 1 SM4 |
| 70 | CH$_2$\CHMe\(CH$_2$)$_3$—N—Tyr—Gly—Gly—Phe—Leu—OH | | | | | | | | K'59 | A1 | 1 SM4 |

TABLE I-continued

| Example No. | Product | $R_f \times 10^2$ | | | | | | | | Process | Footnotes |
|---|---|---|---|---|---|---|---|---|---|---|---|
| | | A | B | C | D | H | P | Q | Other | | |
| 71 | (CH₂)₂\O/(CH₂)₂ Tyr—Gly—Gly—Phe—Leu—OH | | | | | | | | K46 | A1 | 1, SM4 |
| 72 | CH—CH₂\CH₂/ \(CH₂)₂/ Tyr—Gly—Gly—Phe—Leu—OH \CH—CH₂/ | | | | | | | | R30 | A1 | 1, SM4 |

Footnotes
1. Product triturated with diethyl ether and collected by filtration.
2. As 1 but triturated with 50% v/v diethyl ether/petroleum ether (b.p. 60-80° C.).
3. Product obtained as a powder by freeze-drying from water or t-butanol containing 5% v/v of water.
4. Product crystallised from methanol/diethyl ether.
5. Product purified by gel permeation chromatography using Sephadex C15 in 5% v/v aqueous acetic acid.
6. As 5 but using Sephadex G10.
7. As 5 but using 0.1M - ammonium acetate.
8. As 5 but using 0.05M - ammonium hydroxide.
9. As 5 but using Sephadex G10 in 10% v/v aqueous acetic acid.
10. Product purified by column chromatography on silica gel (Merck Kieselgel 7754), eluting with chloroform containing 5% v/v of methanol.
11. As 10 but eluting with chloroform containing 12% v/v of methanol.
12. As 10 but eluting with chloroform containing 15% v/v of methanol.
13. As 10 but eluting with chloroform containing 0 to 2% v/v of methanol, the methanol concentration being increased in a stepwise manner.
14. As 10 and 13 but eluting with chloroform containing 0 to 5% v/v of methanol.
15. As 10 and 13 but eluting with chloroform containing 0 to 10% v/v of methanol.
16. As 10 but eluting with a mixture of chloroform, methanol and water (55:40:1 v/v).
17. As 5 but using Sephadex 1H 20 in methanol.
18. As 5 but using Sephadex G10 in 0.1M - ammonium acetate.
19. As 5 but using Sephadex G10 in 10% w/v ammonium hydroxide.
20. As 5 but using Sephadex G10 in 0.5M - ammonium hydroxide.
21. As 5 but using Sephadex LH 20 in DMF.

Unless otherwise stated below, in those of Examples 1 to 72 in which the products were of the general chemical type:

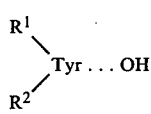

the starting materials had the corresponding general structure:

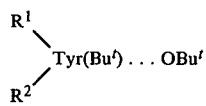

Similarly, unless otherwise stated below, in those of Examples 1 to 72 in which the products were esters or amides of the general chemical type:

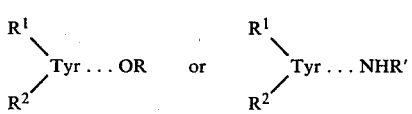

the starting materials has the corresponding general structure:

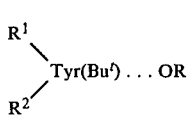

-continued
or

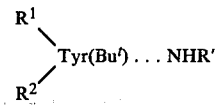

(a) In the case of Example 1, the arginine residue in the starting material was in the form of the N$^\omega$, N$^\epsilon$-bis-adamantyloxycarbonyl derivative.

(b) In the case of Examples 10, 15, 44, 45 and 48, the starting material was of the general chemical type:

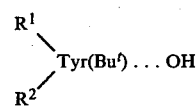

EXAMPLES 73-90

The protecting group(s) in the protected peptide or pseudopeptide was or were removed by cleavage with hydrogen chloride using one of the procedures B1 and B2 described below. The products thus obtained are listed in Table II.

B1. The starting material (0.1 to 10 g.) was dissolved in sufficient 2 M- to 5 M-hydrogen chloride in ethyl acetate to give an approximately 10% w/v solution. The mixture was stirred at 20° to 25° C. for 0.5 to 1 hour, and the product was isolated either by evaporation of the solvent in vacuo or, where appropriate, by the collection of the solid product by filtration.

B2. As B1 but using M-hydrogen chloride in acetic acid.

TABLE II

| Example No. | Product | A | B | C | D | H | P | Q | Others | Process | Foot-notes |
|---|---|---|---|---|---|---|---|---|---|---|---|
| 73 | allyl\Tyr—Gly—Gly—Phe—Gly—OMe/allyl | | | | | | | | $K_{NH_3}85$ | B1 | 1 |
| 74 | allyl\Tyr—Gly—Azgly—NH—△—Ph/allyl | | | | | | | | R60 | B1 | 3 D74 |
| 75 | allyl\Tyr—Gly—Gly—Phe—S—NHCH(Bu$^i$)CH$_2$OH/allyl | 61 | 71 | 62 | | | | | R60 | B1 | 3,15 |
| 76 | allyl\Tyr—Gly—Gly—Phe—NHPh/allyl | | | | | | | | $K_{NH_3}86$ | B1 | 1,14 |
| 77 | allyl\Tyr—Gly—Gly—Phe—NHBzl/allyl | | | | | | | 28 | K86 | B1 | 1,14 SM8 |
| 78 | allyl\Tyr—Gly—Azgly—NHCH$_2$CH$_2$Ph/allyl | | | | | | | 11 | R54 | B1 | 1 |
| 79 | allyl\Tyr—Gly—Azgly—S—NHCHMeCH$_2$Ph/allyl | 61 | 73 | 65 | | | | 20 | R42 | B1 | 3,15 |
| 80 | allyl\Tyr—Gly—Azgly—R,S—NH-(indanyl)/allyl | | | | | | | 14 | R47 | B1 | 3,15 |
| 81 | allyl\Tyr—Gly—NH(CH$_2$)$_2$S(CH$_2$)$_2$Ph/allyl | | | | | | 66 | | $P_{NH_3}31$ | B1 | 3,14 |
| 82 | allyl\Tyr—Gly—Gly—ψ(NHCO)—Phe—Leu—OH/allyl | 68 | 79 | 32 | | | | | K83 | B2 | 3 D82 |
| 83 | allyl\Tyr—Gly—Ser(Bzl)—Phe—Leu—OMe/allyl | | | | | | | 35 | | B1 | 1 D83 |
| 84 | allyl\Tyr—Gly—D-Ser(Bzl)—Phe—Leu—OMe/allyl | | | | | | | 35 | | B1 | 1 |
| 85 | allyl\Tyr—Gly—Gly—Phe—NH(CH$_2$)$_3$CO$_2$Et/allyl | | | | | | | 37 | | B1 | 3 |
| 86 | allyl\Tyr—Gly—Azgly—R—NHCHMeCH$_2$Ph/allyl | | | | | | | 19 | R56 | B1 | 3 D86 |

TABLE II-continued

| Example No. | Product | $R_f \times 10^2$ A | B | C | D | H | P | Q | Others | Process | Foot- notes |
|---|---|---|---|---|---|---|---|---|---|---|---|
| 87 | allyl\\Tyr—Gly—D-Ala—NH(CH$_2$)$_2$Ph/allyl | | | | | | | 25 | R71 | B1 | 3 |
| 88 | allyl\\Tyr—Gly—Gly—NH(CH$_2$)$_2$Ph/allyl | | | | | | | 22 | R62 | B1 | 3 |
| 89 | allyl\\Tyr—Gly—Gly—NH(CH$_2$)$_3$Ph/allyl | | | | | | | 35 | R72 | B1 | 3,14 |
| 90 | allyl\\Tyr—Gly—Gly—Phe—OMe/allyl | | | | | | | Q$_{NH_3}$50 | | B1 | 3 |

The general comments after Examples 1 to 72 concerning the starting materials also apply to Examples 73 to 90. However, in the case of Example 82 the starting material was of the type:

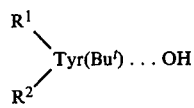

$$\begin{array}{c}R^1\\ \diagdown\\ \phantom{R^1}Tyr(Bu^t)\ldots OH\\ \diagup\\ R^2\end{array}$$

EXAMPLES 91–101

The appropriate ester (see below for information on esters used as starting materials) was hydrolysed by one of the following procedures:

C1. A sufficient quantity of the ester was dissolved in methanol to give a 5 to 20% w/v solution. Aqueous sodium hydroxide (M to 4 M; 2 to 15 molar equivalents) was added, and the mixture was stirred for 0.5 to 2 hours at room temperature. The reaction mixture was neutralised by the addition of an appropriate amount of M-hydrochloric acid, and the solvent was then evaporated in vacuo.

C2. As C1 but using ethanol in place of methanol.

The products thus obtained are listed in Table III. The footnotes in the Table (see the end of Table I for information on the footnotes) indicate how the products were purified.

TABLE III

| Example No. | Product | $R_f \times 10^2$ A | B | C | D | H | P | Q | Other | Process | Foot- notes |
|---|---|---|---|---|---|---|---|---|---|---|---|
| 91 | allyl\\Tyr—Gly—Gly—Phe—Leu—OH/allyl | | | | | | | | K'58 K$_{HOAc}$74 | C1 | 3,9 Ex. 8 |
| 92 | allyl\\Tyr—Gly—Gly—Phe—Leu—OH/Bzl | | | | | | | | K74 K'57 | C1 | 3,19 D92 |
| 93 | allyl\\Tyr—D-Met—Gly—Phe—Leu—OH/allyl | | | | | | | | K69 K'58 | C1 | 3,9,18 Ex. 13 |
| 94 | allyl\\Tyr—D-Ser—Gly—Phe—Leu—OH/allyl | | | | | | | | K82 K'53 | C1 | 3 Ex. 16 |
| 95 | allyl\\Tyr—D-Ser—Gly—Phe—D-Leu—OH/allyl | | | | | | | | K76 K'51 | C1 | 3 Ex. 22 |

TABLE III-continued

| Example No. | Product | A | B | C | D | H | P | Q | Other | Process | Foot- notes |
|---|---|---|---|---|---|---|---|---|---|---|---|
| 96 | allyl\\Tyr—Gly—Sar—Phe—Leu—OH/allyl | 69 | 76 | 33 | | | | | K85 | C1 | 3,20 |
| 97 | allyl\\Tyr—Gly—Gly—Phe(p-NO₂)—Leu—OH/allyl | | | | | | | | K67 K'51 | C1 | 3,9 Ex. 40 |
| 98 | allyl\\Tyr—Gly—Gly—Phe(p-NO₂)—D-Leu—OH/allyl | | | | | | | | K73 K'50 | C1 | 3,17 |
| 99 | allyl\\Tyr—Gly—Gly—Phe—D-Leu—OH/allyl | | | | | | | | K75 K'59 | C1 | 3,17 |
| 100 | allyl\\Tyr—Gly—Gly—Phe—ψ(NHCO)—D,L-Leu—OH/allyl | 57 | 75 | 50 | | | | | K'73 | C2 | 3 Ex. 49 |
| 101 | allyl\\Tyr—Gly—Gly—Phe—Ser(Bzl)—OH/allyl | | | | | 72 | 45 | | | C1 | 1 D101 |

The esters used as starting materials in Examples 91 to 101 were as follows:
Examples 91 to 95, 97 to 99, and 101: the corresponding methyl ester
Example 96: the corresponding benzyl ester
Example 100: the corresponding ethyl ester

EXAMPLES 102 AND 103

Example 102

H-Tyr-Gly-Gly-Phe-Leu-OMe.HCl (0.20 g., 0.33 mM) was dissolved in ethanol (7 ml.). To the solution were added furfuraldehyde (0.031 ml., 0.4 mM), acetic acid (0.016 ml., 0.20 mM) and sodium cyanoborohydride (0.025 g., 0.4 mM). The solution was stirred for 20 hours at room temperature and the solvent was then evaporated in vacuo. The residue was dissolved in a mixture of ethyl acetate (25 ml.) and saturated aqueous sodium bicarbonate solution (20 ml.). The two layers were separated and the organic layer was washed with saturated brine (20 ml.) and dried (Na₂SO₄). The solvent was evaporated in vacuo and the gum-like residue was chromatographed using the dry column chromatography technique with ethyl acetate/methanol (92.5:7.5 v/v). The product band was eluted from the column using ethyl acetate/methanol (85:15 v/v). Evaporation of the solvent in vacuo gave 2-furylmethyl-Tyr-Gly-Gly-Phe-Leu-OMe having R$_f$ 0.3 (t.l.c. on silica gel; chloroform/methanol 92.5:7.5 v/v).

The above-mentioned furylmethyl derivative (0.10 g., 0.15 mM) was dissolved in ethanol (3.5 ml.). To the solution were added acetic acid (0.037 ml., 0.62 mM), propionaldehyde (0.033 ml., 0.46 mM) and sodium cyanoborohydride (0.029 g., 0.46 mM). The solution was stirred for 20 hours at room temperature and the solvent was then evaporated in vacuo. The residue was dissolved in a mixture of ethyl acetate (25 ml.) and saturated aqueous sodium bicarbonate (20 ml.). The two layers were separated and the organic layer was washed with saturated brine (20 ml.) and dried (Na₂SO₄). The solvent was evaporated in vacuo to give a gum-like residue. This residue was chromatographed on two 20×20 cm silica preparative t.l.c. plates using ethyl acetate/methanol 93:7 v/v as eluent. The product band was eluted with ethyl acetate/methanol 80:20 v/v. Evaporation of the solvent in vacuo gave

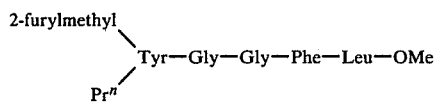

having R$_f$ 0.48 (t.l.c. on silica gel; ethyl acetate/methanol 93:7 v/v).

Example 103

In analogous manner to that described in Example 102 there was obtained bis-(2-furylmethyl)-Tyr-Gly-Gly-Phe-Leu-OMe having R$_f$ 0.44.

EXAMPLE 104

Diallyl-Tyr-Gly-N₂H₃ (462 mg., B 1.01 mM; see D 104) was dissolved in DMF (5 ml.) and the solution was cooled to −20° C. A solution of hydrogen chloride in dioxan (8.0 M, 0.25 ml., 2.0 mM) was added, followed by t-butyl nitrite (138 μl., 1.2 mM), and the mixture was stirred for 3 minutes at −20° C. Triethylamine (0.56 ml., 4.0 mM) was added, followed by a suspension of H-Gly-ψ(-transCH=CH)-D,L-Phe-Leu-OH hydrochloride (300 mg., 0.84 mM; see D104) and triethylamine (238 μl., 1.7 mM) in DMF/H₂O (50% v/v, 10 ml.). The temperature was increased to 0° C. and the pH of the resulting suspension (monitored with moist pH paper) was adjusted to pH 8 by the addition of triethylamine.

Stirring was continued for a further 0.5 hour while maintaining the temperature at 0° C. The pH was again adjusted to 8 by the addition of triethylamine, and the reaction mixture was stirred for a further 24 hours at 0° C. The solvent was evaporated and the residue was partitioned between ethyl acetate (20 ml.) and water (20 ml.). The two phases were separated and the aqueous phase was extracted with more ethyl acetate (20 ml.). The combined ethyl acetate phases were washed successively with water (2×20 ml.) and saturated brine (20 ml.), and then dried (Na$_2$SO$_4$). The solvent was evaporated in vacuo, and the residue was applied to a column of silica (Merck Kieselgel 7754, 24×2.0 cm.) and eluted with chloroform containing 2–5% v/v methanol. The appropriate fractions were combined and the solvent was evaporated in vacuo. The residue was dissolved in t-butanol containing 5% v/v water and the solvent was removed by freeze-drying. There was thus obtained diallyl-Tyr-Gly-Gly-ψ(transCH=CH)-D,L-Phe-Leu-OH, R$_f$R 0.30.

EXAMPLE 105

H-Tyr-D-Met-Gly-Phe-OMe (1.6 g., 4 mM) was dissolved in ethanol/water (9:1 v/v, 25 ml.). To the solution were added sodium bicarbonate (1.008 g., 12 mM) and allyl bromide (1.44 g., 12 mM). The mixture was refluxed for 2 hours. The solvent was evaporated in vacuo and the residue was partitioned between ethyl acetate (50 ml.) and water (50 ml.). The mixture was separated and the organic phase was washed successively with water (50 ml.), M-citric acid (50 ml.), water (50 ml.), M-sodium bicarbonate (50 ml.), water (50 ml.) and saturated brine (50 ml.). The organic phase was then dried (Na$_2$SO$_4$) and the solvent evaporated to give a clear yellow oil. The product was applied to a column of silica (Merck Kieselgel 7754, 24×2.0 cm.) and eluted with chloroform containing 0–2% v/v methanol. The appropriate fractions were combined and the solvent evaporated. The residue was freeze-dried from t-butanol containing 5% v/v water to give dially-Tyr-D-Met-Gly-Phe-OMe, having R$_f$R 0.70.

EXAMPLE 106

DCCI (0.150 g., 0.73 mM) was added to a stirred, cooled (0° C.) solution of diallyl-Tyr-OH (0.181 g., 0.69 mM), H-Gly-D,L-Cys(Bzl)-Phe-Leu-OMe hydrochloride (0.400 g., 0.69 mM), 1-hydroxybenzotriazole (0.187 g., 1.38 mM) and triethylamine (92 μl., 0.69 mM) in DMF (12 ml.). The cooling bath was removed and the reaction mixture was stirred for 16 hours at 20° C. Dicyclohexylurea was removed by filtration and the filtrate was evaporated in vacuo. The residue was partitioned between ethyl acetate (30 ml.) and water (20 ml.). The mixture was separated and the organic phase was washed successively with M-sodium bicarbonate (20 ml.), water (20 ml.), M-citric acid (20 ml.), water (20 ml.) and saturated brine (20 ml.). The organic solution was then dried (MgSO$_4$) and evaporated. The residue was applied to a column of silica (Merck Kieselgel 7754, 30 g.) and eluted with 50% v/v ethyl acetate/petroleum ether (b.p. 60°–80° C.). The appropriate fractions were combined and the solvent was evaporated. The oily residue was freeze-dried from t-butanol containing 5% v/v water to give diallyl-Tyr-Gly-D,L-Cys(Bzl)-PHe-Leu-OMe as a white powder having R$_f$Q 0.45.

EXAMPLE 107

Diallyl-Tyr-Gly-Azgly-OPh (0.200 mg., 0.442 mM) and 2-phenylpropylamine (70.7 μl., 0.486 mM) in methylene dichloride (1 ml.) were stirred for 3 days at 20° C. The solvent was evaporated in vacuo, and the residue was applied to a column of silica (Kieselgel 7754, 1.8×15 cm.) and eluted with chloroform containing 0.5% v/v methanol. The appropriate fractions were combined and the solvent removed by evaporation. The residual glassy solid was freeze-dried from t-butanol containing 5% v/v water to give dially-Tyr-Gly-Azgly-R,S-NHCH$_2$CHMePh as a white powder having R$_f$Q 0.24.

EXAMPLE 108

A solution of diallyl-Tyr-Glyz-Azgly-OPh (0.200 mg., 0.442 mM) and (2S)-2-amino-3-phenyl-1-propanol (73.5 mg., 0.42 mM) in methylene dichloride (1 ml.) was stirred for 2 days at 20° C. The solvent was evaporated in vacuo and the residue was partitioned between ethyl acetate (10 ml.) and water (10 ml.). The mixture was separated and the organic phase was washed successively with 1 M-sodium dihydrogen phosphate (2×5 ml.), water (5 ml.), and saturated brine (5 ml.). The solution was dried (MgSO$_4$) and the solvent removed by evaporation. The residue was applied to a column of silica (Merck Kieselgel 7754, 19×1.5 cm.) and eluted with chloroform containing methanol (0.5% v/v). The appropriate fractions were combined and the solvent was evaporated in vacuo. The residue was freeze-dried from t-butanol containing water (5% v/v) to give diallyl-Tyr-Gly-Azgly-(2S)-NHCH(Bzl)CH$_2$OH as a white powder having R$_f$Q 0.15.

EXAMPLE 109

Diallyl-Tyr-GLy-Gly-Phe-Leu-OMe (55 mg., see Ex. 8) was dissolved in anhydrous ethylamine (5 ml.). The solution was kept at room temperature for 48 hours, and the solvent was then evaporated in vacuo. The residue was diallyl-Tyr-Gly-Gly-Phe-Leu-NHEt having R$_f$D 0.68 and R$_f$Q 0.39.

EXAMPLE 110

A mixture of H-Tyr-Gly-Gly-Phe-Leu-OH (50 mg., 0.09 mM), allyl bromide (1 ml., ca. 100 equivalents), sodium bicarbonate (1 g., ca. 100 equivalents), ethanol (20 ml.) and water (1 ml.) was refluxed for 5 hours. The mixture was cooled to room temperature and filtered, and the solvent was evaporated in vacuo from the filtrate. The residual oily solid was partitioned between ethyl acetate (5 ml.) and 5% v/v aqueous acetic acid (5 ml.). The mixture was separated and the ethyl acetate phase was washed with 5% v/v aqueous acetic acid (2×2 ml.). The combined ethyl acetate phases were dried (MgSO$_4$) and the solvent evaporated in vacuo. The residue was freeze-dried from t-butanol containing 5% v/v water to give diallyl-Tyr-Gly-Gly-Phe-Leu-Oallyl having R$_f$A 0.70, R$_f$C 0.79, R$_f$K 0.94 and R$_f$K' 0.88.

PREPARATION OF STARTING MATERIALS

The peptides and pseudopeptides used as starting materials in the above Examples were obtained by procedures which are conventional in peptide chemistry. By way of illustration, typical preparative procedures are described below (SM1 to SM9). Following that, the preparation of other starting materials is outlined in

SM1

H-Tyr(Bu$^t$)-Gly-Gly-Phe-Leu-OBu$^t$

This compound, which was used in the preparation of various starting materials (see SM2, SM3 and SM4), was obtained as follows:

Z-Gly-OH (25.2 g., 132 mM) was dissolved in DMF (300 ml.) and the solution was cooled to $-10°$ C. N-methylmorpholine (14.8 ml., 132 mM) was added, followed by ethyl chloroformate (12.1 ml., 126 mM). After 3 minutes at $-10°$ C., a solution of H-Phe-Leu-OBu$^t$ (40.1 g., 120 mM) in DMF (100 ml.) was added, and the mixture was stirred at 0° C. overnight. The solvent was evaporated and the residue was dissolved in ethyl acetate (600 ml.) and washed successively with water (2×60 ml.), 2 N-aqueous potassium bicarbonate (3×60 ml.), and water (3×60 ml.). The solution was dried (MgSO$_4$) and filtered. The solvent was evaporated to give Z-Gly-Phe-Leu-OBu$^t$.

The last-named compound (55.7 g., 105 mM) was dissolved in methanol (270 ml.), and 5% palladium-on-carbon catalyst (5 g.) in water (30 ml.) was added. The mixture was vigorously stirred and a slow stream of hydrogen gas was bubbled through it at ambient temperature for 5 hours. The catalyst was filtered off (Kieselguhr) and washed with methanol. The filtrate was evaporated to give H-Gly-Phe-Leu-OBu$^t$ as a white solid.

The last-named compound (29.4 g., 75 mM) was dissolved in DMF (100 ml.), the solution was cooled to 0° C., and Z-Gly-OCP (32.4 g., 83 mM) was added. The mixture was stirred at 0° C. overnight. The solvent was evaporated and the residue was dissolved in ethyl acetate (1 l.), washed with water (5×250 ml.) and then dried (MgSO$_4$). The mixture was filtered and the solvent evaporated. The residue was collected and thoroughly washed with diethyl ether to give Z-Gly-Gly-Phe-Leu-OBu$^t$.

The last-named compound (42 g., 72 mM) was dissolved in methanol (270 ml.) and 5% palladium-on-carbon catalyst (4 g.) in water (30 ml.) was added. The mixture was vigorously stirred and a slow stream of hydrogen gas was bubbled through it at ambient temperature for 5 hours. The catalyst was filtered off (Kieselguhr) and washed with methanol. The filtrate was evaporated to give H-Gly-Gly-Phe-Leu-OBu$^t$.

Z-Tyr(Bu$^t$)-OH dicyclohexylammonium salt (44.2 g., 80 mM) was suspended in ethyl acetate (500 ml.) and the suspension was shaken with 1 N-aqueous citric acid (4×50 ml.) and water (4×50 ml.). The resulting solution in ethyl acetate of Z-Tyr(But)-OH was dried (MgSO$_4$) and filtered, and the solvent was evaporated to give an oil, which was dissolved in DMF (300 ml.). N-Methylmorpholine (9 ml., 80 mM) was added and the solution was cooled to $-10°$ C. Ethyl choroformate (7.2 ml., 76 mM) was added and, after 3 minutes at $-10°$ C., a solution of H-Gly-Gly-Phe-Leu-OBu$^t$ (72 mM, see above) in DMF (100 ml.) was added. The mixture was stirred at $-10°$ C. for 1 hour and then at 0° C. overnight. The solvent was evaporated, the residue was dissolved in ethyl acetate (1 l.) and washed successively with water (2×250 ml.), 1 N-aqueous citric acid (3×150 ml.), water (150 ml.), 2 N-aqueous potassium bicarbonate (3×100 ml.) and water (2×100 ml.). The solution was dried (MgSO$_4$) and filtered and the solvent was evaporated to give Z-Tyr(Bu$^t$)-Gly-Gly-Phe-Leu-OBu$^t$.

The last-named compound (40 g., 50 mM) was hydrogenolyzed as described above to give the required starting material H-Tyr(Bu$^t$)-Gly-Gly-Phe-Leu-OBu$^t$.

SM2

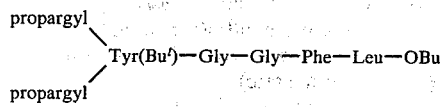

This compound, which was used as the starting material in Example 55, was obtained as follows:

H-Tyr(Bu$^t$)-Gly-Gly-Phe-Leu-OBu$^t$ (0.222 g., 0.33 mM.) was dissolved in ethanol (10 ml.). To the solution were added sodium bicarbonate (0.153 g., 1.65 mM.) and propargyl bromide (0.163 ml., 1.65 mM). The mixture was stirred and refluxed for 20 hours. The solvent was evaporated in vacuo and the residue dissolved in a mixture of ethyl acetate (30 ml.) and water (20 ml.). The two phases were separated and the organic phase was washed with saturated brine (20 ml.) and dried (Na$_2$SO$_4$). The solvent was evaporated in vacuo to give a gum-like residue which was chromatographed using the dry column chromatography technique with ethyl acetate/methanol 97:3 v/v as eluent. The product band was eluted from the column using ethyl acetate/methanol 90:10 v/v. Evaporation of the solvent in vacuo gave dipropargyl-Tyr(Bu$^t$)-Gly-Gly-Phe-Leu-OBu$^t$ as a glassy solid having R$_f$ 0.49 (t.l.c. on silica gel; ethyl acetate/methanol 97:3 v/v).

SM3

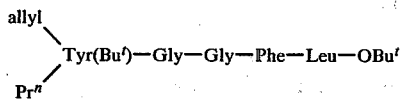

This compound, which was used as the starting material in Example 56, was obtained as follows:

H-Tyr(Bu$^t$)-Gly-Gly-Phe-Leu-OBu$^t$ (2.0 g., 3 mM) was dissolved in ethanol (90 ml.). To the solution were added sodium bicarbonate (0.378 g., 4.5 mM) and allyl bromide (0.387 ml., 4.5 mM). The solution was stirred and refluxed for 20 hours. The solvent was then evaporated in vacuo and the residue dissolved in a mixture of ethyl acetate (120 ml.) and water (80 ml.). The two phases were separated and the organic phase was washed with saturated brine (80 ml.) and dried (Na$_2$SO$_4$). The solvent was evaporated in vacuo to give a gum-like residue which was chromatographed using the dry column chromatography technique with ethyl acetate/methanol 90:10 v/v as eluent. The product band was eluted from the column with ethyl acetate/methanol 85:15 v/v. The solvent was evaporated in vacuo from the eluate to give allyl-Tyr(Bu$^t$)-Gly-Gly-Phe-Leu-OBu$^t$ having R$_f$ 0.48 (t.l.c. on silica gel; ethyl acetate/methanol 90:10 v/v).

The above-mentioned allyl derivative (0.20 g., 0.28 mM) was dissolved in ethanol (10 ml.), and to the solution were added acetic acid (0.050 ml., 0.84 mM), propionaldehyde (0.060 ml., 0.84 mM) and sodium cyanoborohydride (0.035 g., 0.56 mM). The mixture was stirred for 20 hours at room temperature, the solvent was then evaporated in vacuo, and the residue dissolved in a mixture of ethyl acetate (25 ml.) and aqueous sodium bicarbonate (1 M; 20 ml.). The two phases were separated and the organic phase was washed with saturated brine (20 ml.) and dried (Na$_2$SO$_4$). The solvent was evaporated in vacuo and the residue was chromatographed using the dry column chromatography technique with ethyl acetate as the eluent. The product band was eluted from the column using ethyl acetate/methanol 90:10 v/v as the eluent, and evaporation of the solvent in vacuo gave allyl(n-propyl)-Tyr(Bu$^t$)-Gly-Gly-Phe-Leu-OBu$^t$ as a glassy solid having R$_f$0.40 (t.l.c. on silica gel; ethyl acetate).

The following compounds were prepared in analogous manner:

allyl
 \
  Tyr(Bu$^t$)—Gly—Gly—Phe—Leu—OBu$^t$
 /
R

| R | Used as starting material in Example No. |
|---|---|
| Me | 57 |
| Pr$^i$ | 58 |
| Bu$^n$ | 59 |
| phenylethyl | 60 |
| 2-tetrahydrofurylmethyl | 61 |

SM4

The following compounds were prepared in analogous manner to that described in Example 102:

R$^1$
 \
  Tyr(Bu$^t$)—Gly—Gly—Phe—Leu—OBu$^t$
 /
R$^2$

| R$^1$ | R$^2$ | Used as starting material in Example No. |
|---|---|---|
| 2-furylmethyl | Et | 62 |
| 2-furylmethyl | Bu$^n$ | 63 |
| 3-furylmethyl | Pr$^n$ | 64 |
| 3-furylmethyl | 3-furylmethyl | 65 |
| 2-tetrahydrofurylmethyl | Pr$^n$ | 66 |
| 2-tetrahydrofurylmethyl | 2-tetrahydrofurylmethyl | 67 |
| —(CH$_2$)$_5$— | | 68 |
| —(CH$_2$)$_2$—CHMe—(CH$_2$)$_2$— | | 69 |
| —CH$_2$CHMe(CH$_2$)$_3$— | | 70 |
| —(CH$_2$)$_2$—O—(CH$_2$)$_2$— | | 71 |
| —CH$_2$CH(CH$_2$/CH$_2$(CH$_2$)$_2$)CHCH$_2$— | | 72 |

SM5

(allyl)$_2$-Tyr(Bu$^t$)-Gly-Azgly-Phe-Leu-OBu$^t$

This compound, which was used as the starting material in Example 24, was obtained as follows:

H-Phe-Leu-OBu$^t$ (0.669 g., 2 mM) was dissolved in DMF (5 ml.) and the solution was cooled to 0° C. N-carbonyldimidazole (0.33 g., 2 mM) was added and the mixture was stirred for 45 minutes at 0° C. Benzyloxycarbonylglycine hydrazide (0.45 g. 2 mM) was added and the mixture was stirred at 0° C. overnight. The solvent was evaporated and the residue was dissolved in ethyl acetate (100 ml.) and washed with water (3×15 ml.), dried (MgSO$_4$) and filtered. The filtrate was evaporated and the residue was chromatographed on a column of silica gel equilibrated and eluted with methanol/chloroform 1:19 v/v. The product was located by t.l.c. of the fractions from the column. Those which contained pure product were combined and evaporated to give a foam. This was triturated with petroleum ether (b.p. 60°–80° C.) to give Z-Gly-Azgly-Phe-Leu-OBu$^t$.

The last-named compound (0.5 g., 1 mM) was dissolved in methanol (45 ml.), and 5% palladium-on-carbon catalyst (100 mg.) in water (5 ml.) was added. The mixture was vigorously stirred and a slow stream of hydrogen gas was bubbled through it at ambient temperature for 4 hours. The catalyst was filtered off (Kieselguhr) and washed with methanol. The solvent was evaporated from the filtrate and washings and the residue was dried in vacuo over phosphorus pentoxide to give H-Gly-Azgly-Phe-Leu-OBu$^t$ as a foam.

(Allyl)$_2$-Tyr(Bu$^t$)-OH (0.7 g., 2.2 mM) was dissolved in DMF (5 ml.) and the solution was cooled to −10° C. N-methylmorpholine (0.25 ml., 1 equivalent) was added, followed by ethyl chloroformate (0.2 ml., 0.95 equivalent). After 3 minutes at −10° C., a solution of H-Gly-Azgly-Phe-Leu-OBu$^t$ (see above; 0.5 g., 1 mM) in DMF (5 ml.) was added and the mixture was stirred at 0° C. overnight. The solvent was evaporated and the residue was dissolved in ethyl acetate (100 ml.), and washed with water (2×10 ml.), 2 N-aqueous potassium bicarbonate (3×10 ml.) and water (3×10 ml.). The solution was dried (MgSO$_4$) and filtered. The solvent was evaporated to give the crude product which was chromatographed on a column of silica gel equilibrated and eluted with methanol/chloroform 1:19 v/v. The product was located by t.l.c. of the fractions from the column. Those which contained the pure product were combined and evaporated and there was thus obtained (allyl)$_2$-Tyr(Bu$^t$)-Gly-Azgly-Phe-Leu-OBu$^t$.

SM6

(allyl)$_2$-Tyr(Bu$^t$)-Gly-Gly-Phe-ψ(NHCO)-D,L-Leu-OEt

This compound, which was used as the starting material in Example 49, was obtaned as follows:

A. Boc-Gly-Gly-NH-CH(Bzl)-NH$_2$

Boc-Gly-GLy-Phe-OMe (8.0 g., 20 mM) was dissolved in methanol (25 ml.), and 95% v/v hydrazine hydrate (3.2 ml.) was added. The mixture was kept at room temperature for 24 hours and then evaporated. The residue was chromatographed on a column of silica gel equibrated and eluted with methanol/chloroform 1:9 v/v. The fractions which contained the required hydrazide were combined and evaporated to give Boc-Gly-Gly-Phe-NHNH$_2$, R$_f$P 0.6, R$_f$Q 0.3.

The last-named compound (7.9 g., 20 mM) was suspended in 2 N-aqueous hydrochloric acid (30 ml., 3 equivalents) at 0° C. A solution of sodium nitrite (1.52 g., 1.1 equivalents) in water (10 ml.) was then added. The precipitated azide was extracted immediately into ethyl acetate (200 ml.), and the organic phase was washed successively with ice-cold water (2×20 ml.) and 2 N-aqueous potassium bicarbonate (3×15 ml.), and then dried (MgSO$_4$). The solution was filtered from drying agent and warmed gently to 50° C. Benzyl alcohol (17 ml., 10 equivalents) was then added and the mixture was kept at ambient temperature for 24 hours. The solvent was evaporated and the residue was triturated with cyclohexane. The resulting crystalline solid was recrystallised from ethyl acetate/cyclohexane to give Boc-Gly-Gly-NHCH(Bzl)NHCOOBzl, the structure of which was confirmed by NMR.

The last-named compound (1.45 g., 3 mM) was dissolved in DMF (15 ml.) and 5% palladium-on-carbon catalyst (0.2 g.) was added. The mixture was vigorously stirred and a slow stream of hydrogen gas was bubbled through it at ambient temperature for 6 hours. The catalyst was filtered off (Kieselguhr) and washed with DMF (10 ml.). There was thus obtained a solution of Boc-Gly-Gly-NHCH(Bzl)NH$_2$ in DMF ("Solution A").

B. OCP-CO-CH(Bu$^i$)-CO$_2$Et

Ethyl 2-(ethoxycarbonyl)-4-(methyl)pentanoate (6 g., 28 mM) was dissolved in ethanol (9 ml.) and 4 N-aqueous sodium hydroxide (7 ml.) was added. The mixture was stirred at ambient temperature for 1 hour and then evaporated. The residue was diluted with water (30 ml.) and the aqueous solution was washed with diethyl ether (3×10 ml.). The combined ethereal washings were backextracted with water (5 ml.). The combined aqueous phases were acidified to pH 3 at 0° C. with citric acid, and the resulting oil was extracted into ethyl acetate (4×20 ml.). The combined extracts were washed with water (2×20 ml.) and dried (MgSO$_4$). The mixture was filtered and the solvent was evaporated to give 2-ethoxycarbonyl-4-methylpentanoic acid as an oil. The structure was confirmed by NMR.

The said acid (4.7 g., 25 mM) and 2,4,5-trichlorophenol (5.9 g., 30 mM) were dissolved in diethyl ether (100 ml.), and the solution was cooled to 0° C. DCCI (5.2 g., 25 mM) was added and the mixture was stirred at 0° C. for 16 hours. The dicyclohexylurea which was formed was filtered off and washed with diethyl ether. The filtrate and washings were combined and the solvent was evaporated to give an oil. This was purified on a column of silica gel equilibrated and eluted with petroleum ether (60°–80° C.) to give 2-ethoxycarbonyl-4-methyl-pentanoic acid 2,4,5-trichlorophenyl ester as an oil. The structure was confirmed by NMR.

C. Solution A (see section A above) was cooled to 0° C. and the ester named immediately above (2.2 g., 6 mM) was added. The mixture was kept at 0° C. for 16 hours, and the solvent was then evaporated. The residue was dissolved in ethyl acetate (50 ml.), and the crude product was precipitated by the addition of petroleum ether (b.p. 60°–80° C.). The crude product was separated by filtration and purified on a column of silica gel equilibrated and eluted with methanol/chloroform 1:19 v/v. The fractions which contained pure product were combined and evaporated to give Boc-Gly-Gly-Phe-ψ(NHCO)-D,L-Leu-OEt.

The last-named compound (1.2 g., 2 mM) was dissolved in ethyl acetate (50 ml.), and a solution of hydrogen chloride in ethyl acetate (6 molar, 15 ml.) was added. The mixture was kept at ambient temperature for one hour. The solvent was then evaporated and the residue ("compound B") was dried in vacuo over phosphorus pentoxide and sodium hydroxide.

(Allyl)$_2$-Tyr(Bu$^t$)-OH (0.93 g., 2.5 mM) and 1-hydroxybenzotriazole (0.4 g., 3 mM) were dissolved in DMF (3 ml.), and DCCI (0.52 g., 2.5 mM) was added at 0° C. After 15 minutes at 0° C., compound B (2 mM) was added as a suspension in DMF (5 ml.), followed by triethylamine (0.42 ml., 3 mM). The mixture was stirred at 0° C. for 16 hours. The precipitated dicyclohexylurea was filtered off and washed with DMF. The combined filtrate and washings were evaporated and the residue was dissolved in ethyl acetate (75 ml.), washed successively with water (2×15 ml.) and 2N-aqueous potassium bicarbonate (3×15 ml.), and dried (MgSO$_4$). The mixture was filtered and the solvent was evaporated to give an oil. This was purified on a column of silica gel equilibrated and eluted with methanol/chloroform 1:19 v/v. The product was located by t.l.c. of the fractions from the column and those which contained pure product were combined and evaporated to give (allyl)$_2$-Tyr(Bu$^t$)-Gly-Gly-Phe-ψ(NHCO)-D,L-Leu-OEt having $R_fH$ 0.88, $R_fP$ 0.16 and $R_fQ$ 0.34.

SM7

(allyl)$_2$-Tyr(Bu$^t$)-Gly-Gly-ψ(CH$_2$S)-Phe-Leu-OMe

This compound, which was used as the starting material in Example 46, was obtained as follows:

R-2-Bromo-3-phenylpropionic acid (11.46 g., 50 mM), followed by cysteamine hydrochloride (17.04 g., 150 mM), were added to a stirred solution of 0.5 M-aqueous sodium bicarbonate (300 ml.) which was continuously purged with a slow steam of nitrogen. After one hour the reaction flask was sealed and left to stand at room temperature for three days, by which time a white precipitate had separated. The mixture was cooled in an ice-bath and then filtered, and the filtrate was evaporated in vacuo to a small volume. At that stage a solid precipitated. The mixture was filtered and the solid was dissolved in warm water (500 ml.). The solution was applied to a column of cation-exchange resin (BIO-REX 70; H$^+$ form; 20×3.0 cms.). The product was washed from the resin with water (500 ml.), and the solution obtained was evaporated in vacuo until a crystalline solid began to separate. The mixture was set on one side for 16 hours and then filtered. The solid residue was washed with ethanol and then crystallised from ethanol. There was thus obtained H-Gly-ψ(CH$_2$S)-Phe-OH, $[\alpha]_D^{21}$ −6.8° (c 1, in water).

The last-named compound (2.3 g., 10.2 mM) and triethylamine (1.42 ml., 10.2 mM) were dissolved in DMF/water (1:2 v/v; 45 ml.). The solution was cooled to 4° C. and to it was added Boc-Gly-OSu (2.8 g.; 10.2 mM). The mixture was stirred for 16 hours at 4° C. More Boc-Gly-OSu (250 mg.) was added, and stirring was continued for another 16 hours. The solvent was evaporated in vacuo and the oil residue was partitioned between ethyl acetate (100 ml.) and M-aqueous citric acid (100 ml.). The two phases were separated, and the organic phase was washed successively with M-aqueous citric acid (100 ml.) and saturated brine (100 ml.), and then dried (MgSO$_4$). The solution was evaporated in vacuo. The residue was dissolved in 50% v/v aqueous methanol (200 ml.), the solution applied to a column of ion-exchange resin (AG 1-X2; OAc$^-$ form; 16×30 cms.) and eluted with a gradient of 0 to 4% v/v acetic acid in 50% v/v aqueous methanol. The appropriate fractions were combined, the solvent evaporated in vacuo, and the residue was dried in vacuo over sodium hydroxide pellets. There was thus obtained Boc-Gly-Gly-ψ(CH$_2$S)-Phe-OH, the structure of which was confirmed by NMR.

A solution of the last-named compound (2.88 g., 7.5 mM), 1-hydroxybenzotriazole (1.5 g., 11.25 mM) and methyl leucinate hydrochloride (1.5 g. 8.25 mM) in DMF (15 ml.) was stirred at 0° C. To the solution was added a solution of triethylamine (1.15 ml., 8.25 mM) and DCCI (1.75 g., 8.25 mM) in DMF (4 ml.). The mixture was stirred at 4° C. for 48 hours and then filtered. The filtrate was evaporated in vacuo and the residue was partitioned between ethyl acetate (50 ml.) and water (50 ml.). The two phases were separated and the organic phase was washed successively with M-aqueous citric acid (50 ml.), saturated brine (50 ml.), 10% w/v aqueous sodium bicarbonate (50 ml.) and saturated brine (50 ml.), and then dried (MgSO$_4$). The solution was evaporated in vacuo and the residue was purified by column chromatography on silica (Merck Kieselgel 7754; 250 g.) using chloroform containing 0–2.5% v/v of methanol as the eluent. The appropriate fractions were combined and the solvent evaporated in vacuo, and there was thus obtained Boc-Gly-Gly-$\psi$(CH$_2$S)-Phe-Leu-OMe, $R_f P$ 0.46 and $R_f Q$ 0.58.

The last-named compound (1.58 g.) was dissolved in 2 M hydrogen chloride in ethyl acetate (70 ml.), and the solution kept at 23° C. for 1.5 hours. The solvent was evaporated in vacuo, the residue was dissolved in methanol (50 ml.), and the solvent was again removed in vacuo. The residue was mixed with diethyl ether, the solvent was decanted away, and the residual gum was dissolved in 50% v/v aqueous methanol (200 ml.). The solution was passed through a column of an anion-exchange resin (AG 1-X2, OAc$^-$ form). The resulting eluate was applied to a cation-exchange resin (BIO-REX 70; H$^+$ form), and the product was eluted with a gradient of 0–4% v/v acetic acid in 50% v/v aqueous methanol. The product-containing fractions were combined and concentrated by evaporation to yield H-Gly-Gly-$\psi$(CH$_2$S)-Phe-Leu-OMe, $R_f K$ 0.55, $R_f K'$ 0.34.

Isobutyl chloroformate (0.13 ml., 1 mM) was added to a stirred, cooled (−20° C.) solution of (allyl)$_2$-Tyr(Bu$^t$)-OH (320 mg., 1 mM) and N-methylmorpholine (0.11 ml., 1 mM) in THF (10 ml.). The reaction mixture was stirred for 4 minutes at −18° C. A solution of H-Gly-GLy-$\psi$-(CH$_2$S)-Phe-Leu-OMe (470 mg.) and triethylamine (0.14 ml., 1 mM) in THF (10 ml.) and DMF (2 ml.) was added. The reaction mixture was kept at −18° C. for 30 minutes and then at 4° C. for 16 hours. The solvent was evaporated in vacuo and the residue was partitioned between ethyl acetate (25 ml.) and water (25 ml.). The two phases were separated and the organic phase was washed successively with saturated aqueous potassium bicarbonate (25 ml.) and saturated brine (25 ml.), and then dried (MgSO$_4$). The solvent was evaporated and the residue was applied to a column of silica (Merck Kieselgel 7754; 120 g.) and eluted with chloroform containing 0–2.5% v/v methanol. The appropriate fractions were combined and the solvent was evaporated. The residue was dissolved in t-butanol containing 5% v/v water and the solution was freeze-dried. There was thus obtained (allyl)$_2$-Tyr(Bu$^t$)-Gly-Gly-$\psi$(CH$_2$S)-Phe-Leu-OMe having $R_f P$ 0.3 and $R_f Q$ 0.53.

SM8

(Allyl)$_2$-Tyr(Bu$^t$)-Gly-Gly-Phe-NHBzl

This compound, which was used as the starting material in Example 77, was obtained as follows:

Ethyl chloroformate (80 μl., 0.86 mM.) was added to a stirred, cooled (−20° C.) solution of (allyl)$_2$-Tyr(Bu$^t$)-Gly-Gly-Phe-OH (500 mg., 0.86 mM) and N-methylmorpholine (95 μl. 0.86 mM) in DMF (5 ml.). After 1 minute, benzylamine hydrochloride (286 mg., 2.0 mM) was added, followed by N-methylmorpholine (220 μl., 2.0 mM). The reaction mixture was stirred for 1 hour with no further cooling, and the solvent was then evaporated in vacuo. The residue was partitioned between diethyl ether (25 ml.) and saturated aqueous sodium bicarbonate (25 ml.). The two phases were separated and the organic phase was washed successively with water (25 ml.) and saturated brine (25 ml.), and then dried (Na$_2$SO$_4$). The solvent was evaporated in vacuo and the residue was purified on a column of silica (Merck Kieselgel 7754) using 0–2% v/v methanol in chloroform as the eluent. The appropriate fractions were combined and the solvent evaporated in vacuo to give (allyl)$_2$-Tyr(Bu$^t$)-Gly-Gly-Phe-NHBzl.

SM9

(allyl)$_2$-Tyr(Bu$^t$)-Gly-D-Ala-Phe-Leu-OBu$^t$

This compound, which was used as the starting material in Example 27, was obtained as follows:

A. (allyl)$_2$-Tyr(Bu$^t$)-OH

This intermediate was obtained by either of the following alternative procedures:

(1) A mixture of O-t-butyltyrosine (22.41 g., 94.5 mM), sodium bicarbonate (39.64 g., 470 mM) and allyl bromide (40.3 ml., 470 mM) in 10% v/v aqueous methanol (315 ml.) was refluxed for 4 hours. The solvent was removed by evaporation and the residue partitioned between water (150 ml.) and ethyl acetate (300 ml.). The two phases were separated and the organic phase was washed with saturated brine (100 ml.), dried (MgSO$_4$), and concentrated by evaporation to give an oily residue. The residue was purified by column chromatography (silica, eluted with chloroform), and there was thus obtained (allyl)$_2$-Tyr(Bu$^t$)-Oallyl.

Aqueous 2 M-sodium hydroxide (88 ml.) was added to a solution of the last-named compound (57 g., 159 mM) in methanol (400 ml.), and the mixture was heated under reflux. Water was added to the reaction mixture in 20 ml. portions at intervals until no more turbidity was observed (the total volume of water added was approximately 200 ml. over 2 hours). The reaction mixture was then cooled and most of the methanol was removed by evaporation in vacuo. The resulting solution was diluted to 500 ml. with water and washed with diethyl ether (2×100 ml.). The aqueous phase was acidified to pH 4 with solid citric acid and the product was extracted with diethyl ether (2×200 ml.). The combined ethereal extracts were washed with saturated brine (100 ml.), dried (MgSO$_4$), and concentrated by evaporation to give an oily residue. Petroleum ether (b.p. 40°–60° C.; 300 ml.) was added and the mixture was stirred a few minutes until a thick white precipitate had formed. More petroleum ether (b.p. 40°–60° C.; 500 ml.) was added and after trituration the solid was collected by filtration, washed with petroleum ether and dried. There was thus obtained (allyl)$_2$-Tyr(Bu$^t$)-OH, having m.p. 76°–8° C., $R_f$ 0.5 in methanol/chloroform 4:1 by volume and containg 1% v/v acetic acid.

(2) Z-Tyr(Bu$^t$)-OMe (23.7 g.; 61.5 mM) was dissolved in isopropanol (190 ml.). A suspension of 10% palladium-on-charcoal (2.4 g.) was added and a slow stream of hydrogen gas was bubbled through the vigorously stirred reaction mixture which was maintained at room temperature. Throughout the hydrogenolysis a solution of 10% oxalic acid in water (w/v) was added by means of an acetotitrator to maintain a pH of 3. When the theoretical amount of oxalic acid had been consumed the reaction mixture was diluted with water (100 ml.) to dissolve a small amount of solid which had precipitated, and the catalyst was removed by filtration. The filtrate was concentrated by evaporation, the residual white solid was recrystallised from ethanol (100 ml.), and there was thus obtained H-Tyr(Bu$^t$)-OMe monooxalate hemihdyrate, m.p. 155°–6° C.

The last-named compound (13 g.) was partitioned between ethyl acetate (200 ml.) and saturated aqueous sodium bicarbonate (100 ml.). The two phases were separated, the organic phase was dried (MgSO$_4$), and the solvent was evaporated to leave a yellow oil. The oil was dissolved in methanol containing 10% v/v water. Sodium bicarbonate (14.86 g., 177 mM) and allyl bromide (15 ml., 174 mM) were added and the mixture was heated under reflux for 2 hours. The solvent was evaporated in vacuo and the residue was partitioned between water (100 ml.) and diethyl ether (100 ml.). The two phases were separated, both being retained. The aqueous phase was extracted with more diethyl ether (50 ml.). The combined ethereal extracts were washed successively with 20% w/v aqueous citric acid (50 ml.) and saturated brine (50 ml.), and then dried (MgSO$_4$) and concentrated by evaporation to give a yellow oil. The oil was purified by column chromatography (silica; Merck Kieselgel 7734; eluted with chloroform). The appropriate fractions were combined and the solvent removed by evaporation to give (allyl)$_2$-Tyr(Bu$^t$)-OMe.

The last-named compound (7.90 g., 23.86 mM) was dissolved in methanol (35 ml.). Aqueous 2 M-sodium hydroxide (13.20 ml.) was added and the mixture was refluxed for 3 hours. The solvent was removed by evaporation in vacuo. The residual oil was dissolved in water (200 ml.), washed with diethyl ether (3×25 ml.), and acidified with citric acid (6.0 g.). The aqueous phase was saturated with solid sodium chloride and the insoluble oil which separated was extracted into ethyl acetate (3×50 ml.). The combined ethyl acetate extracts were washed successively with water (2×20 ml.), M-aqueous potassium bicarbonate (20 ml.), water (2×20 ml.) and saturated brine (20 ml.). The solution was dried (MgSO$_4$), and the solvent was removed by evaporation in vacuo. The residual oil was triturated with petroleum ether (b.p. 60°–80° C.), whereupon a white solid was formed. The solid was collected by filtration, washed with petroleum ether (b.p. 60°–80° C.), and dried. There was thus obtained (allyl)$_2$-Tyr(Bu$^t$)-OH, having m.p. 70°–78°, R$_f$ 0.5 in methanol/chloroform 4:1 v/v and containing 1% v/v acetic acid.

B. (allyl)$_2$-Tyr(Bu$^t$)-Gly-OMe

This intermediate was obtained by either of the following alternative procedures:

(1) Ethyl chloroformate (4.4 ml., 47.3 mM) was added to a stirred, cooled (−20° C.) solution of (allyl)$_2$-Tyr(Bu$^t$)-OH (14.84 g., 46.67 mM; see section A immediately above) and N-methylmorpholine (5.2 ml., 47.3 mM) in DMF (150 ml.). After 45 seconds methyl glycinate hydrochloride (5.86 g., 46.67 mM) and N-methylmorpholine (5.2 ml. 47.3 mM) were added, and the mixture was stirred for 1.5 hours with no further cooling. Sufficient water was then added to give a clear solution and the solvent was removed by evaporation. The residue was partitioned between ethyl acetate (100 ml.) and water (100 ml.), the two phases were separated, and the ethyl acetate phase was washed successively with aqueous 20% w/v citric acid (50 ml.), saturated aqueous sodium bicarbonate (50 ml.), and saturated brine (50 ml.). The solution was dried (Na$_2$SO$_4$), the solvent was evaporated, and there was thus obtained (allyl)$_2$-Tyr(Bu$^t$)-Gly-OMe.

(2) To a solution of Z-Tyr(Bu$^t$)-Gly-OMe (1.47 g., 3.32 mM) in methanol (20 ml.) was added a suspension of 10% palladium-on-charcoal (180 mg.) in water (5 ml.). The mixture was stirred vigorously and a slow stream of hydrogen was bubbled through it for 3 hours at room temperature. The catalyst was removed by filtration. Allyl bromide (1.42 ml., 16.6 mM) and sodium bicarbonate (1.4 g., 16.6 mM) were added to the filtrate, and the mixture was refluxed for 4.5 hours. The mixture was then cooled to 20° C., and the supernatant liquid was decanted from the precipitated solid. The liquid was concentrated by evaporation. The residue was partitioned between ethyl acetate (30 ml.) and water (20 ml.). The two phases were washed successively with water (2×20 ml.) and saturated brine (20 ml.), dried (Na$_2$SO$_4$), and concentrated by evaporation to give a partially solid residue. This was purified by column chromatography (silica; Merck Kieselgel 7754; eluted with chloroform containing 0 to 2% v/v methanol) and the appropriate fractions were evaporated in vacuo to give (allyl)$_2$-Tyr(Bu$^t$)-Gly-OMe, the structure of which was confirmed by NMR.

C. (allyl)$_2$-Tyr(Bu$^t$)-Gly-OH

Aqueous 2 M sodium hydroxide (22 ml.) was added to a stirred solution of (allyl)$_2$-Tyr(Bu$^t$)-Gly-OMe (15.6 g., 40.3 mM; see section B above) in methanol (150 ml.). After 45 minutes the solvent was removed by evaporation to give a partially solid residue. The residue was partitioned between water (50 ml.) and ethyl acetate (50 ml.). The two phases were separated, and the aqueous phase was acidified with aqueous citric acid (20% w/v, 30 ml.) and extracted with ethyl acetate (4×50 ml.). The combined ethyl acetate extracts were dried (MgSO$_4$) and concentrated by evaporation to leave a clear yellow oil. The oil was dissolved in 50% v/v aqueous methanol and applied to a column of anion exchange resin (AG 1-X2; OAc$^-$ form). The column was eluted with increasing concentrations of acetic acid (0 to 0.5 M increased in stepwise manner) in 50% v/v aqueous methanol, and the fractions containing pure product were combined. The solvent was removed by evaporation to yield a clear yellow oil. The oil was freeze-dried from t-butanol containing 5% v/v water. The freeze-dried solid was dissolved in ethyl acetate (65 ml.), and dicyclohexylamine (7.5 ml.) was added, whereupon a white precipitate slowly formed. This was collected by filtration and washed with ethyl acetate to give the dicyclohexylammonium salt of (allyl)$_2$-Tyr(Bu$^t$)-Gly-OH, m.p. 152°–152.5° C.

D. (allyl)$_2$-Tyr(Bu$^t$)-Gly-D-Ala-Phe-Leu-OBu$^t$

Pivaloyl chloride (0.63 ml., 5.12 mM) was added to a stirred, cooled (−10° C.) suspension of the above-mentioned dicyclohexylammonium salt (2.85 g., 5.14 mM) in DMF (20 ml.). The mixture was stirred for 15 minutes at −10° C. A solution of H-D-Ala-Phe-Leu-OBu$^t$ (2.07 g., 5.10 mM) in DMF (20 ml.) was added and the mixture was stirred for 1 hour at 0° C. and then for 2.5 hrs. at 25° C. Water (100 ml.) was added, the mixture was extracted with ethyl acetate (3×100 ml.), and the combined ethyl acetate extracts were washed successively with 20% w/v aqueous citric acid (50 ml.), saturated aqueous sodium bicarbonate (50 ml.) and saturated brine (100 ml.). The organic solution was dried (MgSO$_4$), and the solvent was evaporated in vacuo. The residue was purified by column chromatography on silica (Merck Kieselgel 7754) and elution with 0–1% v/v methanol in chloroform. The appropriate fractions were combined and the solvent evaporated in vacuo. There was thus obtained (allyl)$_2$-Tyr(Bu$^t$)-Gly-D-Ala-Phe-Leu-OBu$^t$, the structure of which was confirmed by NMR.

D1.
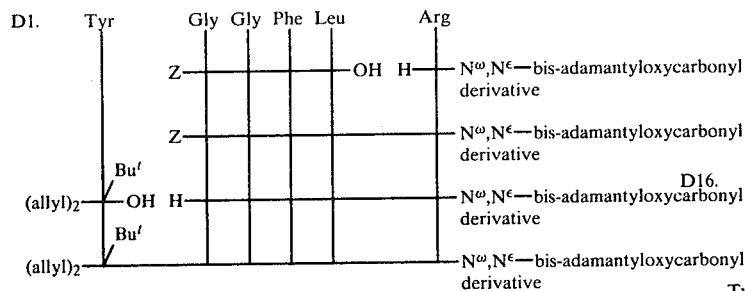

D2.
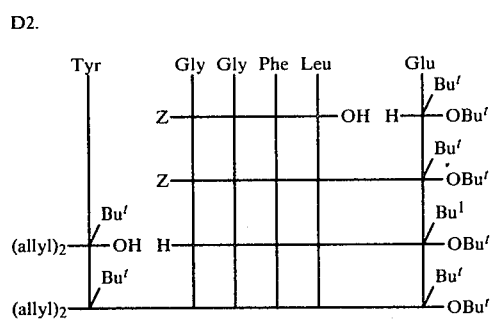

D6.
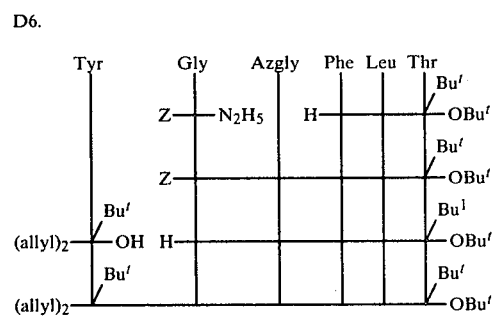

D13.
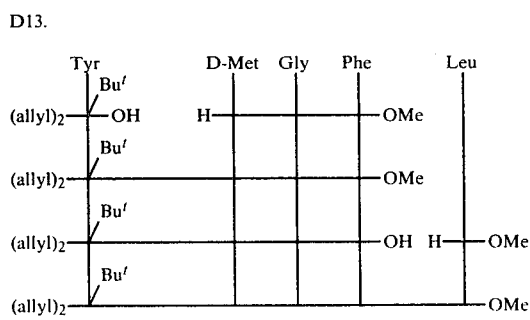

D16.
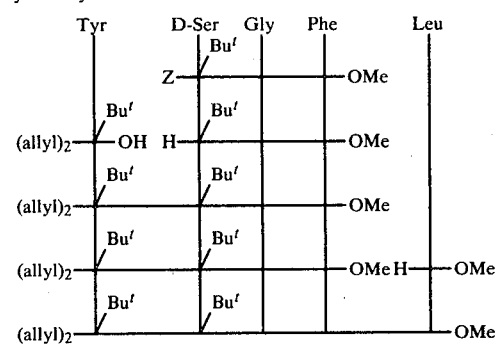

D18
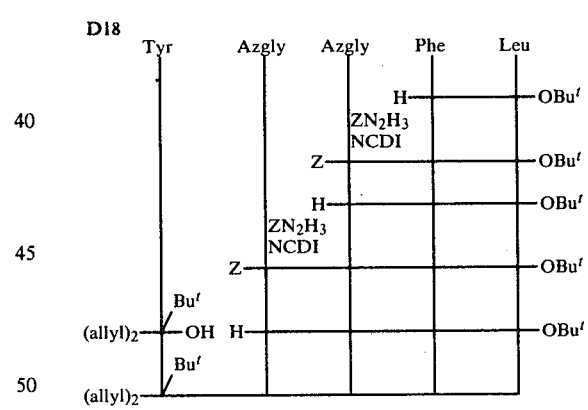

D25.
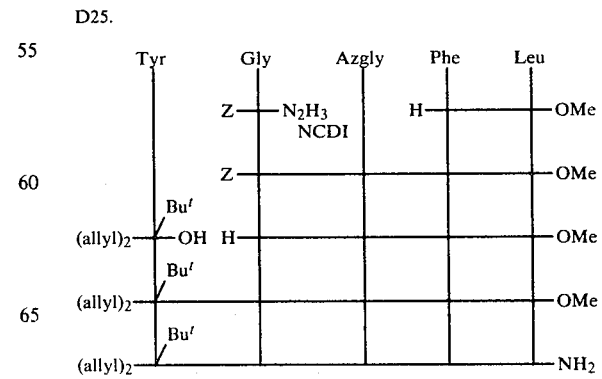

D28.
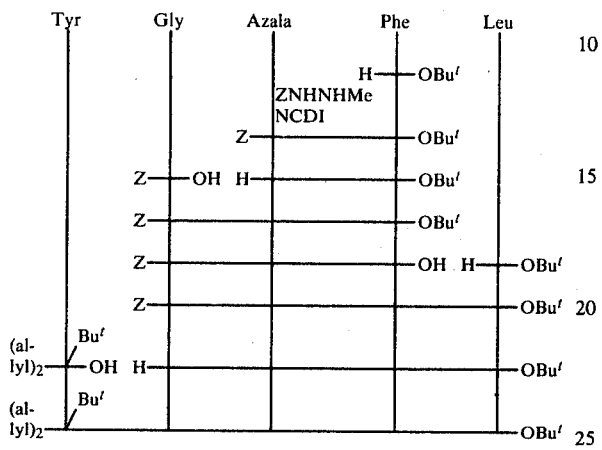
D33.
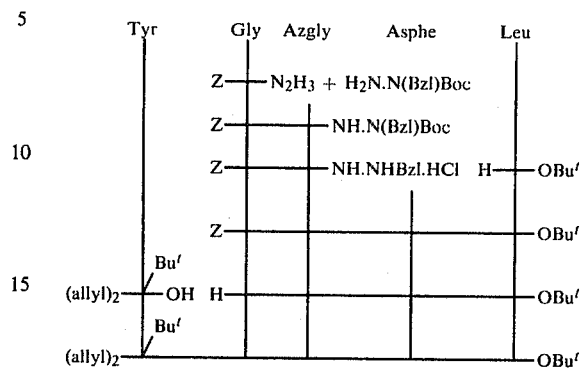
D44.
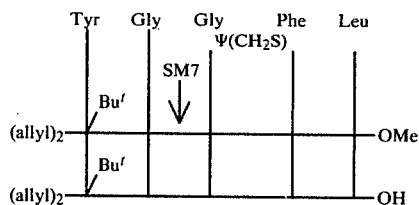
D30.
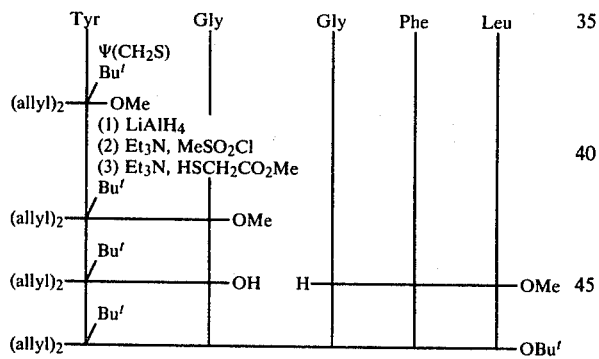
D47.
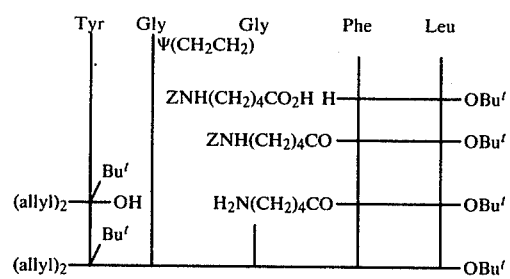
D32.
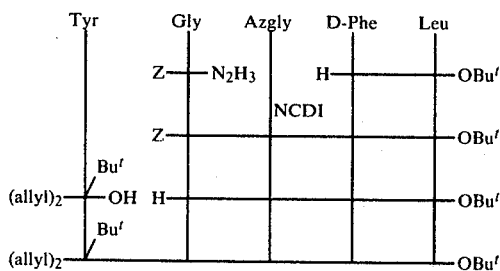
D48.
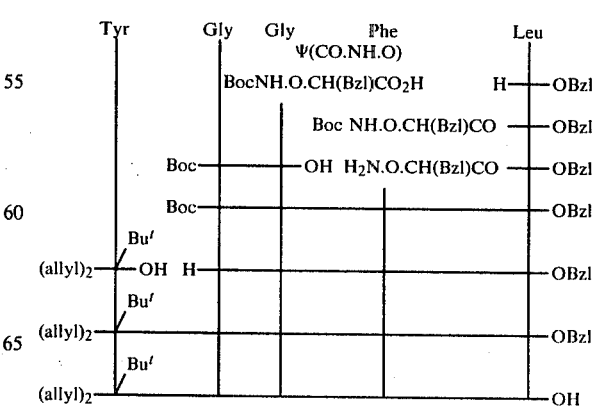

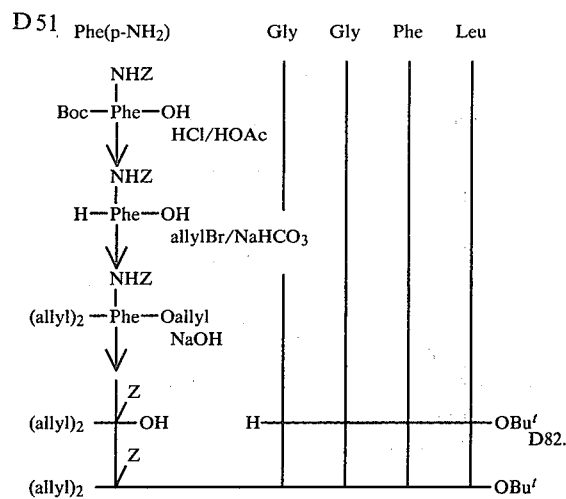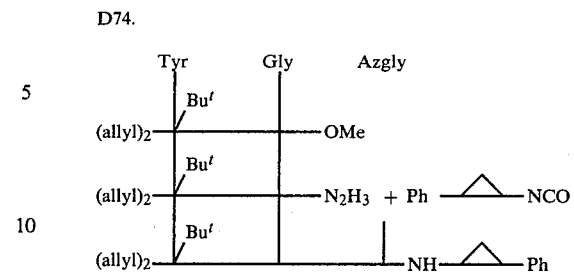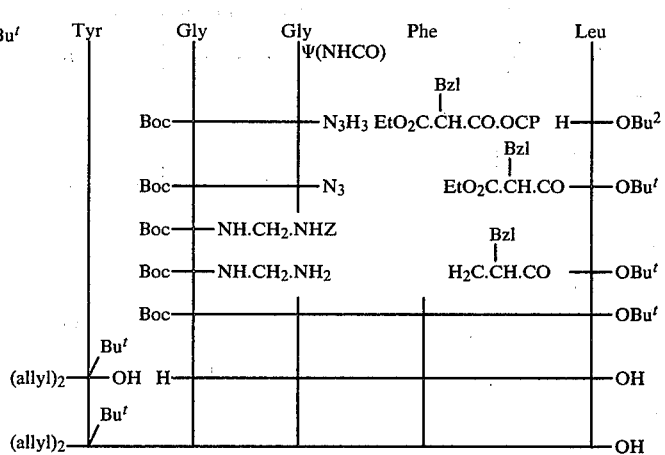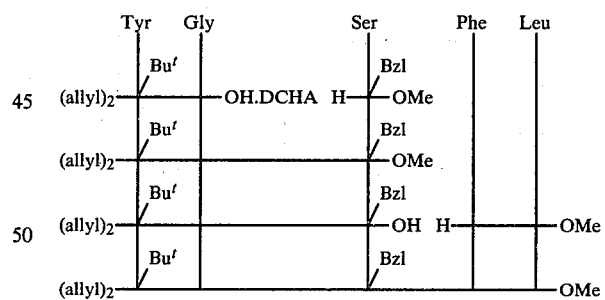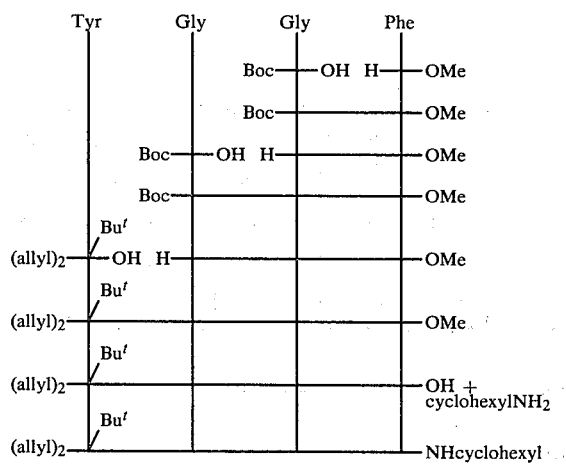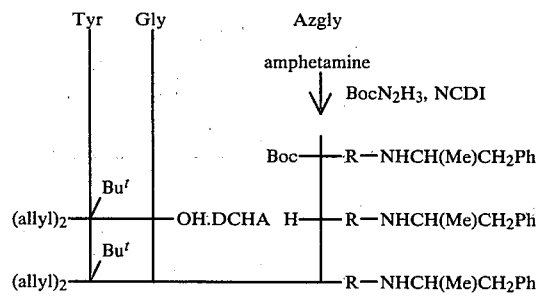

D92.

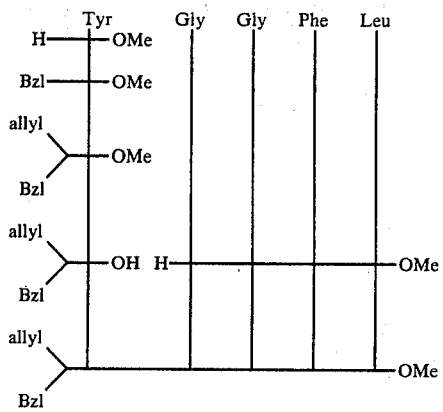

D102.

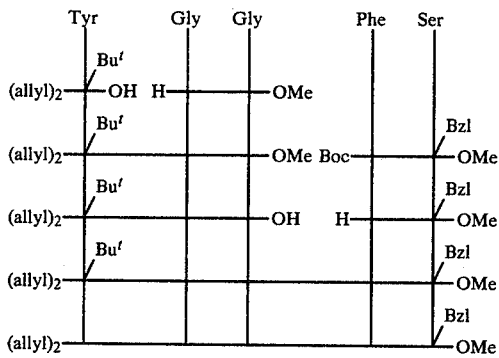

D104.

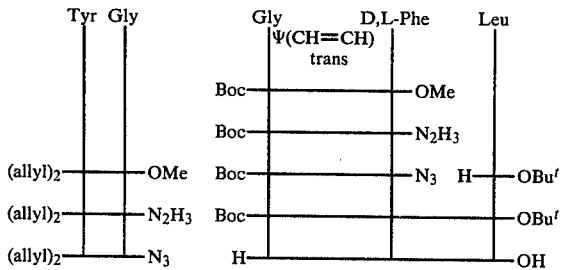

What we claim is:

1. A compound of the formula:

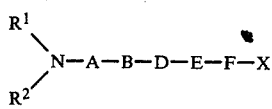

wherein:

$R^1$ stands for an alk-2-enyl, haloalk-2-enyl or alk-2-ynyl radical of not more than 5 carbon atoms, or a furylmethyl or tetrahydrofurylmethyl radical;

$R^2$ stands for an alk-2-enyl, haloalk-2-enyl, alk-2-ynyl or alkyl radical of not more than 5 carbon atoms, a phenylalkyl radical of not more than 10 carbon atoms, or a furylmethyl or tetrahyrofurylmethyl radical;

or $R^1$ and $R^2$ are joined to form, together with the adjacent nitrogen atom, a morpholino, piperidino, methylpiperidino or 1-aza-3,6-methancycloheptan-1-yl radical;

>N-A stands for the residue of D-, L-, D,L- or aza-tyrosine, phenylalanine or p-aminophenylalanine;

B stands for a single valency bond or for the residue of D-, L- or D,L-, where the amino acid contains a chiral centre, or aza-, glycine, methionine, alanine, serine or sarcosine;

D stands for a single valency bond or for the residue of D-, L- or D,L-, where the amino acid contains a chiral centre, or aza-, glycine, alanine, phenylalanine, sarcosine, serine, O-benzylserine, cysteine or S-benzylcysteine;

E stands for a single valency bond or for the residue of D-,L- or D,L-, where the amino acid contains a chiral centre, or aza-, glycine, phenylalanine, N-methylphenylalanine, p-nitrophenylalanine, p-chlorophenylalanine or tryptophan;

F stands for the residue of D-,L- or D,L-, where the amino acid contains a chiral centre, or aza-, glycine, leucine, methionine, alanine, phenylalanine, proline, serine, O-benzylserine or norlecuine, or a dipeptide residue which is D-,L-, D,L- or aza-, leucine-arginine, leucine-glutamic acid, leucine-leucine, leucine-phenylalanine or leucine-threonine; and X stands for a group of the formula $-CO_2R^3$ or $-CONHR^4$, wherein $R^3$ stands for hydrogen or an alkyl or alkenyl radical of not more than 4 carbon atoms, and $R^4$ stands for hydrogen, an alkyl, hydroxyalkyl, cycloalkyl or alkoxycarbonylalkyl radical of not more than 6 carbon atoms, a phenylalkyl or phenyl(hydroxy)alkyl radical of not more than 9 carbon atoms, or a phenyl, phenylcyclopropyl, 2-benzylthioethyl, 2-(2-phenylethylthio)ethyl or indanyl radical;

and wherein the linkages between the amino acid residues are peptide linkages or at least one of said linkages is a pseudo linkage selected from $-CH_2S-$, $-NHCO-$, $-CO.NH.O-$, trans-$CH=CH-$ and $-CH_2CH_2-$;

or a pharmaceutically-acceptable salt thereof.

2. A compound as claimed in claim 1 wherein $R^1$ stands for an allyl, crotonyl, 2-chloroallyl, 3-chloroallyl, propargyl, 2-furylmethyl, 3-furylmethyl or 2-tetrahydrofurylmethyl radical, and $R^2$ stands for an allyl, crotonyl, 2-chloroallyl, 3-chloroallyl, propargyl, methyl, ethyl, n-propyl, n-butyl, benzyl, 2-phenylethyl, 2-furylmethyl, 3-furylmethyl or 2-tetrahydrofurylmethyl radical.

3. A compound as claimed in claim 1 wherein $R^1$ and $R^2$ are joined to form, together with the adjacent nitrogen atom, a morpholino, piperidino, 4-methylpiperidino, 3-methylpiperidino or 1-aza-3,6-methancycloheptan-1-yl radical.

4. A compound as claimed in claim 1 wherein >N-A stands for Tyr or Phe(p-$NH_2$), B stands for a single valency bond or Gly, Azgly, D-Met, D-Ala, D-Ser or Sar, D stands for a single valency bond or Gly, Azgly, Ala, D-Ala, Azala, Phe, D-Phe, Sar, D,L-Ser, Ser, Ser(Bzl), D-Ser(Bzl) or D,L-Cys(Bzl), E stands for a single valency bond or Gly, Phe, D-Phe, Azphe, MePhe, Phe(p-$NO_2$), D,L-Phe(p-Cl) or Trp, and F stands for Gly, Azgly, Leu, D-Leu, D,L-Leu, Met, D-Ala, Phe, Pro, Ser, Ser(Bzl), Nle, Leu-Arg, Leu-Glu, Leu-D-Glu, Leu-Leu, Leu-Phe or Leu-Thr.

5. A compound as claimed in claim 1 wherein $R^3$ stands for hydrogen or a methyl, ethyl or allyl radical.

6. A compound as claimed in claim 1 wherein $R^4$ stands for hydrogen or an ethyl, 4-methyl-2-pentyl, 1-hydroxy-4-methyl-2-pentyl, cyclohexyl, 3-(ethoxycarbonyl)propyl, 2-methoxycarbonyl-2-butyl, benzyl, 2-phenylethyl, 3-phenylpropyl, 1-phenyl-2-propyl, R-1-phenyl-2-propyl, 2-phenylpropyl, 1-hydroxy-3-phenyl-2-propyl, phenyl, phenylcyclopropyl, 2-benzylthioethyl, 2-(2-phenylethylthio)ethyl or 1-indanyl radical.

7. A compounds as claimed in claim 1 wherein $R^1$ and $R^2$ stand for allyl radicals, >N-A stands for Tyr, all of the linkages between the amino acid residues or α-aza-amino-acid residues for peptide linkages or one of said linkages is a psuedo linkage selected from —CH$_2$S—, —NHCO—, —CO.NH.O—, trans —CH=CH— and —CH$_2$CH$_2$—.

8. A compound as claimed in claim 1 which is a member of the group consisting of diallyl-Tyr-Gly-Gly-ψ(CH$_2$S)-Phe-Leu-OH,
diallyl-Tyr-Gly-Azgly-Phe-Leu-OH,
diallyl-Tyr-Gly-Gly-Phe-ψ(NHCO)-D,L-Leu-OEt,
diallyl-Tyr-Gly-Azgly-Phe-Leu-D-Glu-OH, and

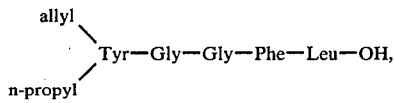

and pharmaceutically-acceptable salts thereof.

9. A pharmaceutical composition suitable for use as an opiate receptor antagonist, comprising an effective amount of a compound of the formula I stated in claim 1, wherein $R^1$, $R^2$, A, B, D, E, F and X have the meanings stated in claim 1, or a pharmaceutically-acceptable salt thereof, and a pharmaceutically-acceptable diluent or carrier.

* * * * *